(12) United States Patent
Goldshleger et al.

(10) Patent No.: US 8,414,564 B2
(45) Date of Patent: Apr. 9, 2013

(54) OPTICAL COHERENCE TOMOGRAPHIC SYSTEM FOR OPHTHALMIC SURGERY

(75) Inventors: Ilya Goldshleger, Irvine, CA (US); Guy Holland, San Clemente, CA (US); Ferenc Raksi, Mission Viejo, CA (US)

(73) Assignee: Alcon LenSx, Inc., Aliso Viejo, CA (US)

( * ) Notice: Subject to any disclaimer, the term of this patent is extended or adjusted under 35 U.S.C. 154(b) by 500 days.

(21) Appl. No.: 12/708,450

(22) Filed: Feb. 18, 2010

(65) Prior Publication Data

US 2011/0202044 A1    Aug. 18, 2011

(51) Int. Cl.
*A61B 18/18* (2006.01)
(52) U.S. Cl. ............................ 606/4; 606/10; 606/18
(58) Field of Classification Search .......... 606/3–6, 606/10–13, 16–19
See application file for complete search history.

(56) References Cited

U.S. PATENT DOCUMENTS

| | | |
|---|---|---|
| 4,164,222 A | 8/1979 | Prokhorov et al. |
| 4,198,143 A | 4/1980 | Karasawa |
| 4,235,529 A | 11/1980 | Kawase et al. |
| 4,465,348 A | 8/1984 | Lang |
| 4,520,816 A | 6/1985 | Schachar et al. |
| 4,533,222 A | 8/1985 | Ishikawa |
| 4,538,608 A | 9/1985 | L'Esperance, Jr. |
| 4,554,917 A | 11/1985 | Tagnon |
| 4,638,801 A | 1/1987 | Daly et al. |
| 4,764,005 A | 8/1988 | Webb et al. |
| 4,881,808 A | 11/1989 | Bille et al. |
| 4,901,718 A | 2/1990 | Bille et al. |
| 4,907,586 A | 3/1990 | Bille et al. |
| 5,048,946 A | 9/1991 | Sklar et al. |
| 5,049,147 A | 9/1991 | Danon |
| 5,054,907 A | 10/1991 | Sklar et al. |
| 5,098,426 A | 3/1992 | Sklar et al. |
| 5,139,022 A | 8/1992 | Lempert |
| 5,246,435 A | 9/1993 | Bille et al. |

(Continued)

FOREIGN PATENT DOCUMENTS

| | | |
|---|---|---|
| EP | 1444946 A1 | 8/2004 |
| JP | 2002345758 | 12/2002 |

(Continued)

OTHER PUBLICATIONS

PCT International Search Report and Written Opinion dated Feb. 9, 2012 for International Application Serial No. PCT/US2011/040223.

(Continued)

*Primary Examiner* — Mohammed Hasan

(57) ABSTRACT

Optical imaging techniques and systems provide high-fidelity optical imaging based on optical coherence tomographic imaging and can be used for optical imaging in ophthalmic surgery and imaging-guided surgery. One method for imaging an eye includes positioning the eye relative to a Spectral Domain Optical Coherence Tomographic (SD-OCT) imaging system, the eye having a first and a second structure, and imaging the eye with the SD-OCT imaging system by selecting one of a direct image and a mirror image of the first eye-structure and generating a first image-portion corresponding to the selected image of the first eye-structure, selecting one of a direct image and a mirror image of the second eye-structure and generating a first image-portion corresponding to the selected image of the second eye-structure, and suppressing the non-selected images of the first and second structures.

44 Claims, 26 Drawing Sheets

U.S. PATENT DOCUMENTS

| | | | |
|---|---|---|---|
| 5,255,025 A | 10/1993 | Volk | |
| 5,286,964 A | 2/1994 | Fountain | |
| 5,321,501 A | 6/1994 | Swanson et al. | |
| 5,336,215 A | 8/1994 | Hsueh et al. | |
| 5,391,165 A | 2/1995 | Fountain et al. | |
| 5,439,462 A | 8/1995 | Bille et al. | |
| 5,493,109 A | 2/1996 | Wei et al. | |
| 5,549,632 A | 8/1996 | Lai | |
| 5,656,186 A | 8/1997 | Mourou et al. | |
| 5,738,676 A | 4/1998 | Hammer et al. | |
| 5,779,696 A | 7/1998 | Berry et al. | |
| 5,795,295 A | 8/1998 | Hellmuth et al. | |
| 5,936,706 A | 8/1999 | Takagi | |
| 5,954,648 A | 9/1999 | Van Der Brug | |
| 5,954,711 A | 9/1999 | Ozaki et al. | |
| 5,994,690 A | 11/1999 | Kulkarni et al. | |
| 6,004,314 A | 12/1999 | Wei et al. | |
| 6,095,648 A | 8/2000 | Birngruber et al. | |
| 6,099,522 A | 8/2000 | Knopp et al. | |
| 6,137,585 A | 10/2000 | Hitzenberger et al. | |
| 6,254,595 B1 | 7/2001 | Juhasz et al. | |
| 6,288,784 B1 | 9/2001 | Hitzenberger et al. | |
| 6,314,311 B1 | 11/2001 | Williams et al. | |
| 6,317,616 B1 | 11/2001 | Glossop | |
| 6,337,925 B1 | 1/2002 | Cohen et al. | |
| 6,377,349 B1 | 4/2002 | Fercher | |
| 6,379,005 B1 | 4/2002 | Williams et al. | |
| 6,451,009 B1 | 9/2002 | Dasilva et al. | |
| 6,454,761 B1 | 9/2002 | Freedman | |
| 6,497,701 B2 | 12/2002 | Shimmick et al. | |
| 6,529,758 B2 | 3/2003 | Shahidi | |
| 6,579,282 B2 | 6/2003 | Bille et al. | |
| 6,623,476 B2 | 9/2003 | Juhasz et al. | |
| 6,687,010 B1 | 2/2004 | Horii et al. | |
| 6,730,074 B2 | 5/2004 | Bille et al. | |
| 6,741,359 B2 | 5/2004 | Wei et al. | |
| 6,751,033 B2 | 6/2004 | Goldstein et al. | |
| 6,755,819 B1 | 6/2004 | Waelti | |
| 6,763,259 B1 | 7/2004 | Hauger et al. | |
| 6,769,769 B2 | 8/2004 | Podoleanu et al. | |
| 6,775,007 B2 | 8/2004 | Izatt et al. | |
| 6,863,667 B2 | 3/2005 | Webb et al. | |
| 6,887,232 B2 | 5/2005 | Bille | |
| 6,899,707 B2 | 5/2005 | Scholler et al. | |
| 6,932,807 B1 | 8/2005 | Tomita et al. | |
| 6,991,629 B1 | 1/2006 | Juhasz et al. | |
| 6,996,905 B2 | 2/2006 | Meguro | |
| 7,006,232 B2 | 2/2006 | Rollins et al. | |
| 7,018,376 B2 | 3/2006 | Webb et al. | |
| 7,027,233 B2 | 4/2006 | Goldstein et al. | |
| 7,061,622 B2 | 6/2006 | Rollins et al. | |
| 7,072,047 B2 | 7/2006 | Westphal et al. | |
| 7,079,254 B2 | 7/2006 | Kane et al. | |
| 7,102,756 B2 | 9/2006 | Izatt et al. | |
| 7,113,818 B2 | 9/2006 | Podoleanu et al. | |
| 7,126,693 B2 | 10/2006 | Everett et al. | |
| 7,130,054 B2 | 10/2006 | Ostrovsky et al. | |
| 7,133,137 B2 | 11/2006 | Shimmick | |
| 7,139,077 B2 | 11/2006 | Podoleanu et al. | |
| 7,145,661 B2 | 12/2006 | Hitzenberger | |
| 7,148,970 B2 | 12/2006 | de Boer | |
| 7,184,148 B2 | 2/2007 | Alphonse | |
| 7,207,983 B2 | 4/2007 | Hahn et al. | |
| 7,248,371 B2 | 7/2007 | Chan et al. | |
| 7,268,885 B2 | 9/2007 | Chan et al. | |
| 7,280,221 B2 | 10/2007 | Wei | |
| 7,307,733 B2 | 12/2007 | Chan et al. | |
| 7,310,150 B2 | 12/2007 | Guillermo et al. | |
| 7,312,876 B2 | 12/2007 | Chan et al. | |
| 7,319,566 B2 | 1/2008 | Prince et al. | |
| 7,329,002 B2 | 2/2008 | Nakanishi | |
| 7,330,270 B2 | 2/2008 | O'Hara et al. | |
| 7,330,273 B2 | 2/2008 | Podoleanu et al. | |
| 7,335,223 B2 | 2/2008 | Obrebski | |
| 7,336,366 B2 | 2/2008 | Choma et al. | |
| 7,342,659 B2 | 3/2008 | Horn et al. | |
| 7,347,548 B2 | 3/2008 | Huang et al. | |
| 7,352,444 B1 | 4/2008 | Seams et al. | |
| 7,355,716 B2 | 4/2008 | de Boer et al. | |
| 7,364,296 B2 | 4/2008 | Miller et al. | |
| 7,365,856 B2 | 4/2008 | Everett et al. | |
| 7,365,859 B2 | 4/2008 | Yun et al. | |
| 7,370,966 B2 | 5/2008 | Fukuma et al. | |
| 7,371,230 B2 | 5/2008 | Webb et al. | |
| 7,372,578 B2 | 5/2008 | Akiba et al. | |
| 7,388,672 B2 | 6/2008 | Zhou et al. | |
| 7,390,089 B2 | 6/2008 | Loesel et al. | |
| 7,400,410 B2 | 7/2008 | Baker et al. | |
| 7,402,159 B2 | 7/2008 | Loesel et al. | |
| 7,426,037 B2 | 9/2008 | Ostrovsky et al. | |
| 7,433,046 B2 | 10/2008 | Everett et al. | |
| 7,452,077 B2 | 11/2008 | Meyer et al. | |
| 7,452,080 B2 | 11/2008 | Wiltberger et al. | |
| 7,461,658 B2 | 12/2008 | Jones et al. | |
| 7,466,423 B2 | 12/2008 | Podoleanu et al. | |
| 7,470,025 B2 | 12/2008 | Iwanaga | |
| 7,477,764 B2 | 1/2009 | Haisch | |
| 7,480,058 B2 | 1/2009 | Zhao et al. | |
| 7,480,059 B2 | 1/2009 | Zhou et al. | |
| 7,488,070 B2 | 2/2009 | Hauger et al. | |
| 7,488,930 B2 | 2/2009 | Ajgaonkar et al. | |
| 7,492,466 B2 | 2/2009 | Chan et al. | |
| 7,503,916 B2 | 3/2009 | Shimmick | |
| 7,508,525 B2 | 3/2009 | Zhou et al. | |
| 7,535,577 B2 | 5/2009 | Podoleanu et al. | |
| 7,537,591 B2 | 5/2009 | Feige et al. | |
| 7,557,928 B2 | 7/2009 | Ueno | |
| 7,575,322 B2 | 8/2009 | Somani | |
| 7,593,559 B2 | 9/2009 | Toth et al. | |
| 7,602,500 B2 | 10/2009 | Izatt et al. | |
| 7,604,351 B2 | 10/2009 | Fukuma et al. | |
| 7,614,744 B2 | 11/2009 | Abe | |
| 7,630,083 B2 | 12/2009 | de Boer et al. | |
| 7,631,970 B2 | 12/2009 | Wei | |
| 7,633,627 B2 | 12/2009 | Choma et al. | |
| 7,643,152 B2 | 1/2010 | de Boer et al. | |
| 7,813,644 B2 | 10/2010 | Chen et al. | |
| 7,898,712 B2 | 3/2011 | Adams et al. | |
| 2001/0022648 A1 | 9/2001 | Lai | |
| 2002/0013574 A1 | 1/2002 | Elbrecht et al. | |
| 2002/0082466 A1 | 6/2002 | Han | |
| 2002/0097374 A1 | 7/2002 | Payne et al. | |
| 2002/0133145 A1 | 9/2002 | Gerlach et al. | |
| 2002/0198516 A1 | 12/2002 | Knopp | |
| 2003/0090674 A1 | 5/2003 | Zeylikovich et al. | |
| 2003/0206272 A1 | 11/2003 | Cornsweet et al. | |
| 2004/0039378 A1 | 2/2004 | Lin | |
| 2004/0059321 A1 | 3/2004 | Knopp et al. | |
| 2004/0151466 A1 | 8/2004 | Crossman-Bosworth et al. | |
| 2004/0243233 A1 | 12/2004 | Phillips | |
| 2005/0010109 A1 | 1/2005 | Faul | |
| 2005/0015120 A1 | 1/2005 | Seibel et al. | |
| 2005/0021011 A1 | 1/2005 | LaHaye | |
| 2005/0173817 A1 | 8/2005 | Fauver et al. | |
| 2005/0192562 A1 | 9/2005 | Loesel et al. | |
| 2005/0201633 A1 | 9/2005 | Moon et al. | |
| 2005/0203492 A1 | 9/2005 | Nguyen et al. | |
| 2005/0215986 A1 | 9/2005 | Chernyak et al. | |
| 2005/0284774 A1 | 12/2005 | Mordaunt | |
| 2005/0286019 A1 | 12/2005 | Wiltberger et al. | |
| 2005/0288745 A1 | 12/2005 | Andersen et al. | |
| 2006/0020172 A1 | 1/2006 | Luerssen et al. | |
| 2006/0077346 A1 | 4/2006 | Matsumoto | |
| 2006/0100613 A1 | 5/2006 | McArdle et al. | |
| 2006/0179992 A1 | 8/2006 | Kermani | |
| 2006/0187462 A1 | 8/2006 | Srinivasan et al. | |
| 2006/0195076 A1 | 8/2006 | Blumenkranz et al. | |
| 2006/0206102 A1 | 9/2006 | Shimmick | |
| 2007/0013867 A1 | 1/2007 | Ichikawa | |
| 2007/0121069 A1 | 5/2007 | Andersen et al. | |
| 2007/0126985 A1 | 6/2007 | Wiltberger et al. | |
| 2007/0129709 A1 | 6/2007 | Andersen et al. | |
| 2007/0129775 A1 | 6/2007 | Mordaunt et al. | |
| 2007/0147730 A1 | 6/2007 | Wiltberger et al. | |
| 2007/0173791 A1 | 7/2007 | Raksi | |
| 2007/0173794 A1 | 7/2007 | Frey et al. | |
| 2007/0173795 A1 | 7/2007 | Frey et al. | |

| | | | |
|---|---|---|---|
| 2007/0185475 | A1 | 8/2007 | Frey et al. |
| 2007/0189664 | A1 | 8/2007 | Andersen et al. |
| 2007/0216909 | A1 | 9/2007 | Everett et al. |
| 2007/0219541 | A1 | 9/2007 | Kurtz |
| 2007/0230520 | A1 | 10/2007 | Mordaunt et al. |
| 2007/0282313 | A1 | 12/2007 | Huang et al. |
| 2007/0291277 | A1 | 12/2007 | Everett et al. |
| 2007/0299429 | A1 | 12/2007 | Amano |
| 2008/0033406 | A1 | 2/2008 | Andersen et al. |
| 2008/0049188 | A1 | 2/2008 | Wiltberger et al. |
| 2008/0055543 | A1 | 3/2008 | Meyer et al. |
| 2008/0056610 | A1 | 3/2008 | Kanda |
| 2008/0071254 | A1 | 3/2008 | Lummis et al. |
| 2008/0088795 | A1 | 4/2008 | Goldstein et al. |
| 2008/0100612 | A1 | 5/2008 | Dastmalchi et al. |
| 2008/0281303 | A1 | 11/2008 | Culbertson et al. |
| 2008/0281413 | A1 | 11/2008 | Culbertson et al. |
| 2008/0319427 | A1 | 12/2008 | Palanker |
| 2009/0012507 | A1 | 1/2009 | Culbertson et al. |
| 2009/0088734 | A1 | 4/2009 | Mordaunt |
| 2009/0125005 | A1 | 5/2009 | Chernyak et al. |
| 2009/0131921 | A1 | 5/2009 | Kurtz et al. |
| 2009/0149742 | A1* | 6/2009 | Kato et al. ............ 600/425 |
| 2009/0157062 | A1 | 6/2009 | Hauger et al. |
| 2009/0161827 | A1 | 6/2009 | Gertner et al. |
| 2009/0168017 | A1 | 7/2009 | O Hara et al. |
| 2009/0268161 | A1 | 10/2009 | Hart et al. |
| 2010/0004641 | A1 | 1/2010 | Frey et al. |
| 2010/0004643 | A1 | 1/2010 | Frey et al. |
| 2010/0007848 | A1 | 1/2010 | Murata |
| 2010/0022994 | A1 | 1/2010 | Frey et al. |
| 2010/0022995 | A1 | 1/2010 | Frey et al. |
| 2010/0022996 | A1 | 1/2010 | Frey et al. |
| 2010/0042079 | A1 | 2/2010 | Frey et al. |
| 2010/0110377 | A1 | 5/2010 | Maloca et al. |
| 2010/0324543 | A1 | 12/2010 | Kurtz et al. |
| 2011/0022036 | A1 | 1/2011 | Frey et al. |
| 2011/0118609 | A1 | 5/2011 | Goldshleger et al. |
| 2011/0319873 | A1 | 12/2011 | Raksi et al. |

FOREIGN PATENT DOCUMENTS

| | | |
|---|---|---|
| WO | 98/08048 | 2/1998 |
| WO | 9808048 | 2/1998 |
| WO | 2006074469 | 7/2006 |
| WO | WO2007106326 | 9/2007 |
| WO | 2007130411 | 11/2007 |

OTHER PUBLICATIONS

Hee et al.; "Femotosecond transillumination optical coherence tomography"; Optics Letters; vol. 18; No. 12; pp. 950-952 (Jun. 1993).

Kamensky et al.; "In situ monitoring of the middle IR laser ablation of a cataract-suffered human lens by optical coherent tomography"; Proc. SPIE; 2930: 222-229 (1996).

Kamensky et al.; "Monitoring and animation of laser ablation process in cataracted eye lens using coherence IDS 41 tomography"; Proc. SPIE; 2981: 94-102 (1997).

Ostaszewski et al.; "Risley prism beam pointer"; Proc. of SPIE; vol. 6304; 630406-1 through 630406-10.

PCT International Search Report for International Application Serial No. PCT/US2010/056701 mailed Aug. 24, 2011.

Swanson et al.; "In vivo retinal imaging by optical coherence tomography"; Optics Letters; vol. 18; No. 21; pp. 1864-1866 (Nov. 1993).

Chinn, S.R., et al., "Optical coherence tomography using a frequency-tunable optical source," Optics Letters, 22(5):340-342, Mar. 1997.

Huber, R., et al., "Three-dimensional and C-mode OCT imaging with a compact, frequency swept laser source at 1300 nm," Optics Express, 13(26):10523-10538, Dec. 2005.

Massow, O., et al., "Femtosecond laser microsurgery system controlled by optical coherence tomography," Proceedings of the SPIE—Commercial and Biomedical Applications of Ultrafast Lasers VIII, vol. 6881, pp. 688106(1)-688106(6), Mar. 2008.

Massow, O., et al., "Optical coherence tomography controlled femtosecond laser microsurgery system," Proceedings of the SPIE—Optical Coherence Tomography and Coherence Techniques III, vol. 6627, pp. 662717(1)-662717(6), Aug. 2007.

Ohmi, M., et al., "In-situ Observation of Tissue Laser Ablation Using Optical Coherence Tomography," Optical and Quantum Electronics, 37(13-15):1175-1183, Dec. 2005.

Sarunic, M., et al., "Imaging the Ocular Anterior Segment With Real-Time, Full-Range Fourier-Domain Optical Coherence Tomography," Archives of Ophthalmology, 126(4):537-542, Apr. 2008.

Sarunic, M., et al., "Instantaneous complex conjugate resolved spectral domain and swept-source OCT using 3×3 fiber couplers," Optics Express, 13(3):957-967, Feb. 2005.

Sarunic, M. et al., "Real-time quadrature projection complex conjugate resolved Fourier domain optical coherence tomography," Optics Letters, 31(16):2426-2428, Aug. 2006.

Swanson, et al., "Method and Apparatus for Optical Imaging with Means for Controlling the Longitudinal Range of the Sample," Re-exam U.S. Appl. No. 90/006,816, filed Oct. 20, 2003.

Tao, Y., et al., "High-speed complex conjugate resolved retinal spectral domain optical coherence tomography using sinusoidal phase modulation," Optics Letters, 32(20):2918-2920, Oct. 2007.

Yun, S.H., et al., "Wavelength-swept fiber laser with frequency shifted feedback and resonantly swept intra-cavity acoustooptic tunable filter," IEEE Journal of Selected Topics in Quantum Electronics, 3(4):1087-1096, Aug. 1997.

International Search Report and Written Opinion dated Mar. 12, 2009 for International Application No. PCT/US2008/075511, filed Sep. 5, 2008 (9 pages).

European Patent Office, European Patent Application No. 10191057.8, in European Search Report, mailed Mar. 16, 2011, to be published by the USPTO, 3 pages.

RE 90/006,816, Feb. 27, 2007, Swanson et al.

Arimoto et al., "Imaging Properties of Axicon in a Scanning Optical System," Nov. 1, 1992, Applied Optics, 31(31): 6652-6657, 5 pages.

Birngruber et al., "In-Vivo Imaging of the Development of Linear and Non-Linear Retinal Laser Effects Using Optical Coherence Tomography in Correlation with Histopathological Findings," 1995, Proc. SPIE 2391:21-27, 7 pages.

Stern et al., "Femtosecond Optical Ranging of Corneal Incision Depth," Jan. 1989, Investigative Ophthalmology & Visual Science, 30(1):99-104, 6 pages.

Fercher et al., "Eye-Length Measurement by Interferometry With Partially Coherent Light," Mar. 1988, Optics Letters, 13(3):186-188, 3 pages.

Fercher et al., "Measurement of Intraocular Distances by Backscattering Spectral Interferometry," May 15, 1995, Optics Comm. 117:43-48, 6 pages.

Wojtkowski et al., "In Vivo Human Retinal Imaging by Fourier Domain Optical Coherence Tomography," Jul. 2002, Journal of Biomedical Optics 7(3):457-463, 7 pages.

Izatt et al., Micron-Resolution Biomedical Imaging With Optical Coherence Tomography, Oct. 1993, Optics & Photonics News, pp. 14-19, 6 pages.

Kim, Tae Hoon, Authorized Officer, Korean Intellectual Property Office, PCT International Application No. PCT/US2011/023710, in International Search Report, mailed Aug. 24, 2011, 8 pages.

Kim, Tae Hoon, Authorized Officer, Korean Intellectual Property Office, PCT International Application No. PCT/US2011/025332, in International Search Report, mailed Sep. 16, 2011, 8 pages.

Partial International Search Report corresponding to PCT Application Serial No. PCT/US2012/035927 dated Aug. 3, 2012.

PCT International Search Report and Written Opinion dated Apr. 10, 2012 for International Application No. PCT/US2011/051466, filed Sep. 13, 2011.

* cited by examiner

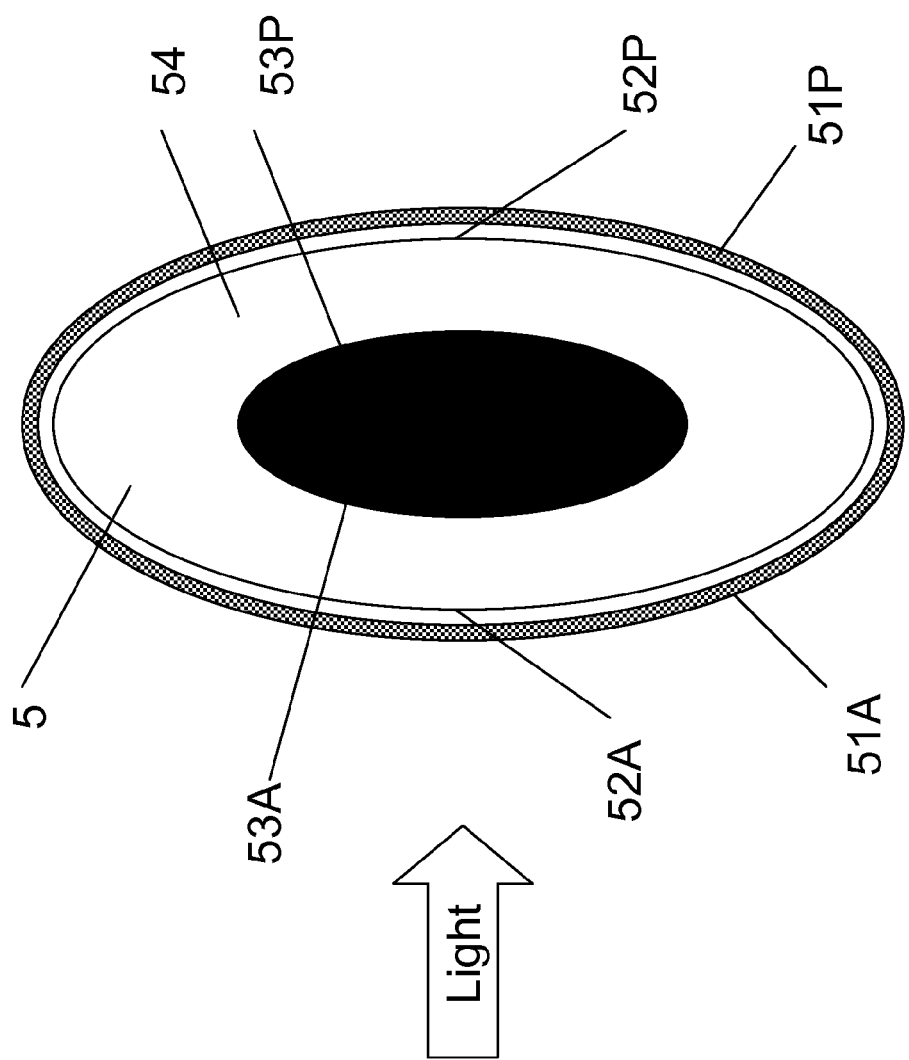

FIG. 3A

- 110 — positioning the eye relative to a Spectral Domain Optical Coherence Tomographic (SD-OCT) imaging system
- 120 — imaging the eye with the SD-OCT imaging system by
- 130 — selecting one of a direct image and a mirror image of the first eye-structure and generating a first image-portion, corresponding to the selected image of the first eye-structure
- 140 — selecting one of a direct image and a mirror image of the second eye-structure and generating a second image-portion, corresponding to the selected image of the second eye-structure
- 150 — suppressing the non-selected images of the first and second eye-structures

100

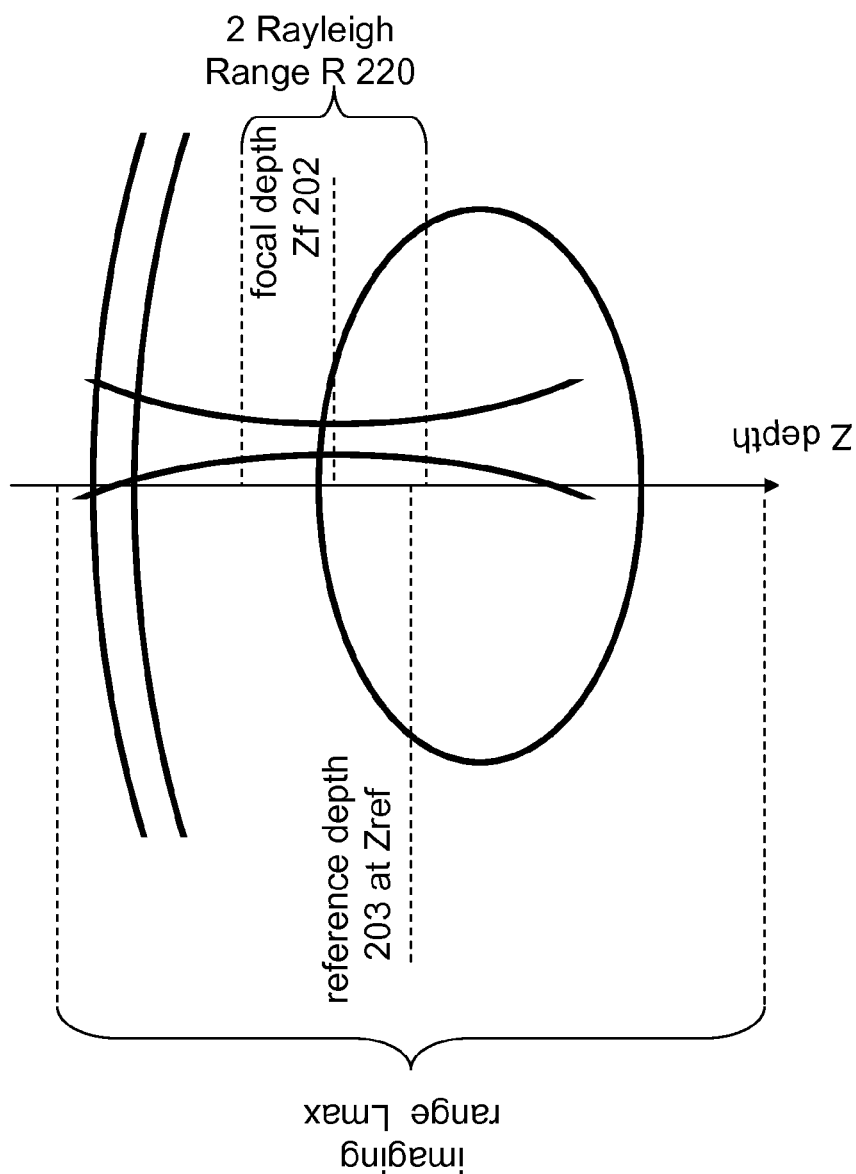

OPTICAL COHERENCE TOMOGRAPHIC SYSTEM FOR OPHTHALMIC SURGERY

TECHNICAL FIELD

This patent document relates to imaging techniques and systems, including optical coherence tomographic imaging systems for ophthalmic surgery.

BACKGROUND

The eye can develop numerous problems, especially for a person of an advanced age, and such problems can diminish the efficiency or precision of its vision. Ophthalmic medicine aspires to improve the deteriorated functions of the eye. One of serious eye-diseases is the development of a cataract that can cause clouding of the lens and loss of the lens transparency and lead to loss of vision. A major goal of cataract surgery is to replace the dysfunctional natural lens with an artificial lens, restoring the vision of the eye.

SUMMARY

Optical imaging techniques and systems described in this document provide high-fidelity optical imaging based on optical coherence tomographic imaging and can be used for, among other applications, optical imaging in ophthalmic surgery and imaging-guided surgery.

For example, a method for imaging an eye can include the steps of: positioning the eye relative to a Spectral Domain Optical Coherence Tomographic (SD-OCT) imaging system, the eye having a first and a second structure; and imaging the eye with the SD-OCT imaging system by selecting one of a direct image and a mirror image of the first eye-structure and generating a first image-portion, corresponding to the selected image of the first eye-structure; selecting one of a direct image and a mirror image of the second eye-structure and generating a second image-portion, corresponding to the selected image of the second eye-structure; and suppressing the non-selected images of the first and second structures.

In some implementations the suppressing the non-selected images step includes at least one of: preventing the display of generated non-selected images, generating the non-selected images without displaying the non-selected images, or performing a computational step to prevent the generation of the non-selected images.

In some implementations the generating the first and second image-portions includes performing a transformation on one of the first and second image-portions to generate a biologically representative image of the first and second structures, when at least one of the first and the second image-portions is a mirror image.

In some implementations the imaging the eye step includes adjusting a reference depth of the SD-OCT imaging system to generate the direct and mirror images of the first and second eye-structures at corresponding image depths so that the direct and mirror images of the first and second eye-structures can be distinguished from each other.

In some implementations the distinguishing the direct and mirror images of the first and second eye-structures step includes at least one of: recognizing a spatial separation of the images, applying a pattern recognition approach, distinguishing a signal characteristic of the images, utilizing pre-existing knowledge about the eye, or utilizing knowledge about the eye based on a diagnostics.

In some implementations the steps of adjusting the reference depth and distinguishing the direct and mirror images of the first and second eye-structures are performed iteratively.

In some implementations the first structure is an anterior capsule layer of a lens of the eye and the second structure is a posterior capsule layer of the lens of the eye.

In some implementations the imaging the eye step includes adjusting the reference depth of the SD-OCT imaging system so that a depth-sequence of the first image-portion, the second image-portion and a cornea image is one of: direct image of the cornea—direct image of the anterior capsule layer—mirror image of the posterior capsule layer; direct image of the cornea—mirror image of the posterior capsule layer—direct image of the anterior capsule layer; and mirror image of the posterior capsule layer—direct image of the cornea—direct image of the anterior capsule layer.

In some implementations the imaging the eye step includes adjusting the reference depth of the SD-OCT imaging system so that a depth-sequence of the first image-portion, the second image-portion and a cornea image is one of: mirror image of the cornea—mirror image of the anterior capsule layer—direct image of the posterior capsule layer; mirror image of the cornea—direct image of the posterior capsule layer—mirror image of the anterior capsule layer; and direct image of the posterior capsule layer—mirror image of the cornea—mirror image of the anterior capsule layer.

In some implementations the adjusting the reference depth step includes adjusting a position of a reference mirror of the SD-OCT imaging system; and tuning a delay element of the SD-OCT imaging system.

In some implementations the imaging the eye step includes a homodyne imaging.

In some implementations the imaging the eye step includes adjusting an imaging range around the reference depth to result in the first and the second structures being located within the imaging range.

In some implementations the adjusting the imaging range step includes adjusting at least one of a central wavelength and a wavelength resolution of the SD-OCT imaging system.

In some implementations the adjusting step includes adjusting the imaging range to be within the 0-15 mm range.

In some implementations the adjusting step includes adjusting the imaging range to be in the 5-15 mm range.

In some implementations the imaging the eye step includes adjusting a Rayleigh range around a focal depth to result in the imaging range being less than 4 times the Rayleigh range.

In some implementations the adjusting the reference depth step includes adjusting the reference depth to be within the range of 2-15 mm.

In some implementations the positioning the eye step includes at least one of docking the eye to an interface of the SD-OCT imaging system, immobilizing the eye, or minimizing a motion range of the eye relative to the SD-OCT imaging system.

In some implementations the SD-OCT imaging system is one of Spectrometer Based OCT (SB-OCT) and a Swept Source OCT (SS-OCT) imaging system.

In some implementations the imaging of the eye includes at least one of creating a single z-scan, creating a planar z-scan, creating a z-scan along a scanning line, or creating a z-scan in a raster pattern.

In some implementations an imaging system for imaging an eye includes a Spectral Domain Optical Coherence Tomographic (SD-OCT) imaging system that positions the eye relative to the SD-OCT imaging system, the eye having a first and a second structure; generates a first image-portion, selected from a direct image and a mirror image of the first structure; generates a second image-portion, selected from a direct image and a mirror image of the second structure; and suppresses non-selected images of the first and second structures.

In some implementations, the SD-OCT imaging system includes an imaging light source that outputs an imaging light; one or more beam splitters that splits the imaging light into an imaging beam and a reference beam; and unifies a returned imaging light-portion and a returned reference light-portion into an interfering light; a reference device, that returns the reference light-portion, with a time difference proportional to a reference distance; and an interference analyzer, that receives the interfering light; and generates an SD-OCT image of the eye.

In some implementations the SD-OCT is one of a Spectrometer Based OCT (SB-OCT) and a Swept Source OCT (SS-OCT).

In some implementations the reference device is configured so that the returned reference light-portion is one of advanced or delayed relative to the returned imaging light-portion.

In some implementations the reference distance of the reference mirror is related to a reference depth in the eye, wherein the interference analyzer has a maximum imaging sensitivity at the reference depth.

In some implementations the first structure is an anterior capsule layer of a lens of the eye; the second structure is a posterior capsule layer of the lens of the eye; the reference distance is adjustable to set the reference depth so that a depth-sequence of the first image-portion, the second image-portion and an image of a cornea is one of mirror image of the posterior capsule layer—direct image of the anterior capsule layer—direct image of a cornea; direct image of the anterior capsule layer—mirror image of the posterior capsule layer—direct image of the cornea; and direct image of the anterior capsule layer—direct image of the cornea—mirror image of the posterior capsule layer.

In some implementations the first structure is an anterior capsule layer of a lens of the eye; the second structure is a posterior capsule layer of the lens of the eye; the reference distance is adjustable to set the reference depth so that a depth-sequence of the first image-portion, the second image-portion and an image of a cornea is one of direct image of the posterior capsule layer—mirror image of the anterior capsule layer—mirror image of a cornea; mirror image of the anterior capsule layer—direct image of the posterior capsule layer—mirror image of the cornea; and mirror image of the anterior capsule layer—mirror image of the cornea—direct image of the posterior capsule layer.

In some implementations the reference distance is adjustable to control the reference depth to within the range of 2-15 mm.

In some implementations the SD-OCT imaging system controls an imaging range around the reference depth into a range of one of 0 mm-15 mm and 5 mm-15 mm.

In some implementations the SD-OCT imaging system suppresses the non-selected images by at least one of preventing the display of generated non-selected images; generating the non-selected images without displaying the non-selected images; or performing a computational step to prevent the generation of the non-selected images.

In some implementations the method includes the steps of: positioning the object relative to a Spectral Domain Optical Coherence Tomographic (SD-OCT) imaging system, where the object includes a high contrast structure in a low contrast medium; generating an image of the high contrast structure with the SD-OCT imaging system, corresponding to one of a direct image and a mirror image of the high contrast structure; and suppressing a non-selected image of the high contrast structure.

In some implementations the generating the image of the high contrast structure step includes adjusting a reference depth of the SD-OCT imaging system to generate the image of the high contrast structure at an image depth so that the image of the high contrast structure is distinguishable from a first image of a first structure.

In some implementations, the adjusting the reference depth step includes distinguishing the image of the high contrast structure from the first image by at least one of recognizing a spatial separation of the image of the high contrast structure from the first image; applying a pattern recognition approach; distinguishing a signal characteristic of the image of the high contrast structure and the first image; utilizing pre-existing knowledge about the object; or utilizing a knowledge about the object based on a diagnostics.

In some implementations the generating an image of the high contrast structure step includes a homodyne imaging.

In some implementations the generating an image of the high contrast structure step includes setting a reference depth of the SD-OCT imaging system and adjusting an imaging range around the reference depth to result in the imaging range covering the high contrast structure.

In some implementations the adjusting the imaging range step includes adjusting at least one of a central wavelength and a wavelength resolution of the SD-OCT imaging system to result in the imaging range covering the high contrast structure.

In some implementations the adjusting the imaging range step includes adjusting the imaging range to be within one of a range of 0 mm-15 mm and 5 mm-15 mm.

In some implementations the adjusting the imaging range step includes adjusting the reference depth to be within a range of 2 mm-15 mm.

In some implementations the adjusting the imaging range step includes adjusting a focal depth of the SD-OCT imaging system and adjusting a Rayleigh range around the focal depth of the SD-OCT imaging system to result in the imaging range being less than 4 times the Rayleigh range.

In some implementations a surgical laser system includes a surgical laser delivery system and a Spectral Domain Optical Coherence Tomographic (SD-OCT) imaging system, coupled to the surgical laser delivery system, wherein the SD-OCT imaging system images an object having a high contrast structure in a low contrast medium, generates an image of the high contrast structure corresponding to one of a direct image and a mirror image of the high contrast structure and suppresses a non-selected image of the high contrast structure.

In some implementations, the SD-OCT imaging system includes an imagining light source to output an imaging light, one or more beam splitter that splits the imaging light into an imaging beam and a reference beam and unifies a returned imaging beam-portion and a returned reference beam-portion into an interference beam, a reference mirror, that returns the reference beam-portion, positioned at a reference distance, and an interference analyzer, that receives the interference beam and generates an SD-OCT image of the eye.

In some implementations the SD-OCT is one of a Spectrometer Based OCT (SB-OCT) and a Swept Source OCT (SS-OCT).

In some implementations the reference distance of the reference mirror is related to a reference depth in the eye, wherein the interference analyzer has a maximum imaging sensitivity at the reference depth.

In some implementations the reference distance is adjustable to control the reference depth to within the range of 2-15 mm.

In some implementations the SD-OCT imaging system is configured to control an imaging range around the reference depth into a range of one of 0 mm-15 mm and 5 mm-15 mm.

In some implementations the SD-OCT imaging system suppresses the non-selected image by at least one of preventing the display of generated non-selected image, generating the non-selected images without displaying the non-selected image, or performing a computational step to prevent the generation of the non-selected image.

The above and other aspects of the technique and systems for optical imaging are described in detail in the drawings, the description and the claims.

BRIEF DESCRIPTION OF THE DRAWINGS

FIGS. 1A-B illustrate the main structural components of an eye.

FIG. 3A illustrates the steps of an exemplary imaging method.

FIG. 5B illustrates a relationship between the imaging range, the reference depth, the focal depth and the Rayleigh range.

DETAILED DESCRIPTION

Figure 1A:
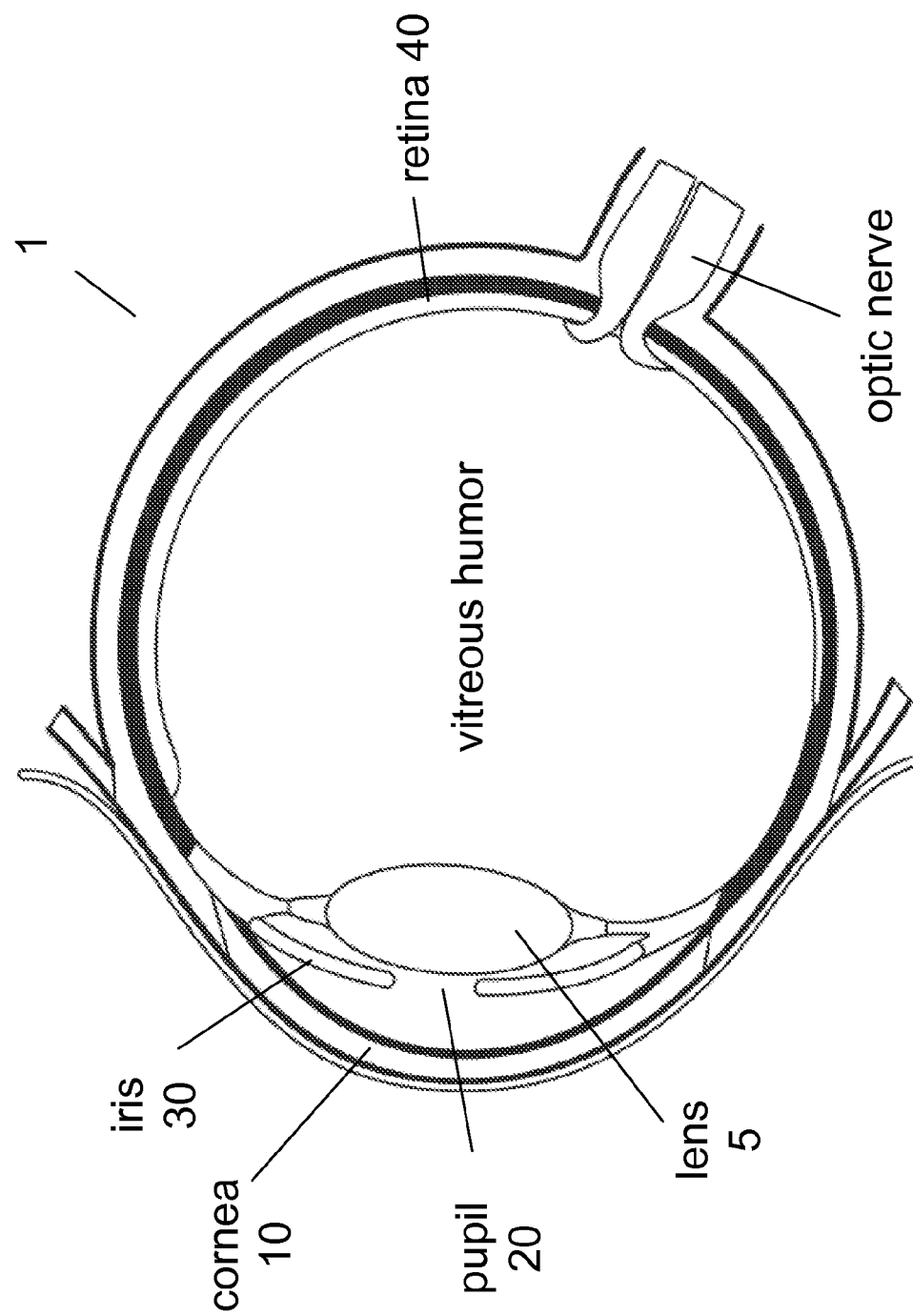

FIG. 1A illustrates a typical human eye 1. The well known main structural elements of the eye 1 include a lens 5, a cornea 10, a pupil 20, an iris 30, a retina 40, the central chamber of the eye being filled up with a vitreous humor, and the visual stimulations of the retina departing for the brain through the optic nerve.

FIG. 1B illustrates a side view of the lens 5 itself more closely. In finer detail, the lens 5 is contained in a capsule 51, whose thickness is typically of the order of 20 microns. The capsule has a capsule anterior surface 51A and a capsule posterior surface 51P, using the direction of the incident light as a reference axis. The lens is defined by a lens anterior surface 52A and lens posterior surface 52P. Inside the lens 5 a hard nucleus 53 exhibits the cataractous loss of transparency, embedded in a softer outer shell, sometimes called cortex 54. The total extent of the lens depends on several factors, including the age of the patient. Its z-extent can vary in the range of 6-8 mm, and its radial extent (transverse to the z axis) is of the order of 5 mm. The cataractous portion, typically the hard nucleus 53, often has a z-extent of 2-6 mm, depending on many factors.

In cataract surgery the hard nucleus 53 is typically cut, chopped or fragmented by inserted surgical devices, often aided by the application of ultrasound in the course of the so-called phaco technology. The pieces or fragments of the hard nucleus 53 as well as the softer and more fluid cortex 54 are then subsequently removed from the capsule 51 through a circular opening on the lens anterior surface 52A and the capsule 51 by applying vacuum suction. This circular opening is formed by a process called capsulotomy, or capsulorhexys. The surgery is completed by inserting an Intra Ocular Lens (IOL) into the empty capsule 51 to restore the optical performance and indeed vision of the eye.

Over the last forty years cataract surgery was performed primarily with hand-held surgical tools, aided by ultrasound phaco devices and/or heated fluid devices. Given the sensitive target of the surgery, substantial effort has been focused on developing ophthalmic surgical systems with increased precision. Only very recently was it attempted to replace the traditional tools with surgical laser systems. These laser systems promise dramatically better precision when cutting the capsule 51 and nucleus 53: a precision of few microns instead of a few hundred microns or even millimeters, typical for the phaco technologies.

The precision of laser-based cataract surgical systems can be enhanced by integrating an imaging system with the surgical laser system. Such an imaging system can determine the location of the lens anterior and lens posterior surfaces 52A-52P with high precision to guide lens-surgical processes.

These lens-surgical processes include capsulotomy, capsulorhexys and capsulo-lysis. The precision of the capsulotomy is a key factor controlling the centration of the IOL. The centration is essential to optimize the performance of the inserted IOL, because an off-center placement of the IOL can cause astigmatisms or other optical distortions in the operated eye. The precision of the lens chopping is comparably important to make sure that the entire lens is properly fragmented.

A particularly efficient imaging technique is called optical coherence tomography, or OCT. In the OCT technique an imaging light is split into an image beam and a reference beam. These beams are returned to the imaging system by the imaged object and a reference mirror and are united into a combined interference beam. This interference beam can be analyzed in the time domain or in the frequency domain, the two main realizations of OCT techniques.

However, even the OCT technique is hampered by various drawbacks and thus improvements of the OCT technique are needed to increase the efficiency of the laser-based cataract surgical systems.

A well known challenge of the OCT technique is the so-called "complex ambiguity". This problem emerges because the interference pattern is related to the magnitude square of the sum of the interfering image beam and reference beam and thus exhibits Hermitean symmetry. Put another way, when a light wave is detected, only the amplitude is recorded and the phase information is lost. Thus, a wave and its complex conjugate generate the same interference pattern. This creates an ambiguity when attempting to re-construct the original light wave. Unable to resolve this ambiguity, OCT imaging systems generate both a direct image of the targeted object as well as a mirror image, an artifact of the complex ambiguity.

Figure 2:
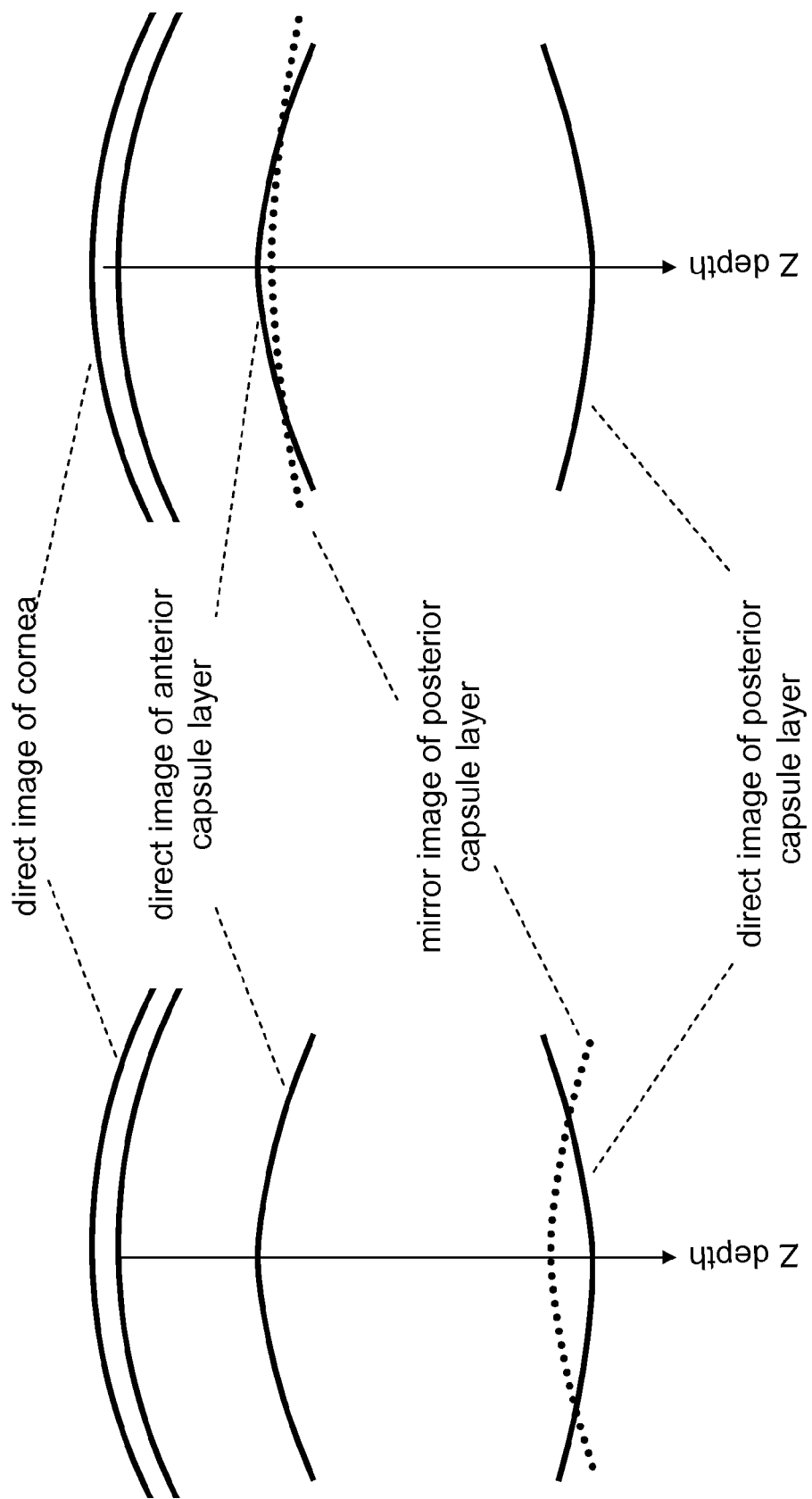
FIG. 2 illustrates the complex ambiguity problem of OCT imaging.

FIG. 2 illustrates the complex ambiguity problem which can arise from the duplication of images in OCT. The left panel shows the case when the mirror image of the posterior capsule layer overlaps with the direct image of the posterior capsule layer. The right panel shows the case when the mirror image of the posterior capsule layer overlaps with the direct image of the anterior capsule layer. In either case these overlapping images cannot be distinguished and result in ambiguity, possibly confusing the surgeon and thus endangering the success of the ophthalmic procedure. This challenge of the complex ambiguity perplexed system designers up to now as existing methods are unable to resolve the ambiguity and isolate and generate the direct image of the targeted object, while there is a pressing need to image both the anterior and the posterior capsule layers precisely to guide the capsulotomy and the fragmenting of the lens.

Optical imaging techniques and systems described in this document provide high-fidelity optical imaging based on optical coherence tomographic imaging and can be used in, among other applications, optical imaging in ophthalmic surgery and imaging-guided surgery. The described optical imaging techniques and systems can be implemented in ways that mitigate technical problems associated with the complex ambiguity in OCT.

FIG. 3A illustrates an implementation of a method 100 to provide images for ophthalmic surgical applications which remove the complex ambiguity of the OCT technique.

Some embodiments of the method 100 for imaging an eye include the steps of:

(110)—positioning the eye relative to a Spectral Domain Optical Coherence Tomographic (SD-OCT) imaging system, the eye having a first and second structure; and (120)—imaging the eye with the SD-OCT imaging system by (130)—selecting one of a direct image and a mirror image of the first eye-structure and generating a first image-portion, corresponding to the selected image of the first eye-structure;

(140)—selecting one of a direct image and a mirror image of the second eye-structure and generating a second image-portion, corresponding to the selected image of the second eye-structure; and (150)—suppressing the non-selected images of the first and second eye-structures. These steps will be described below in detail.

Here and throughout the present patent document the terms "image" and "eye-structure" can refer to a partial image and a partial eye-structure as OCT scanning typically images only portions of a full target and thus the generated image is typically a partial image, representing a portion of the eye-structure. As such, a single image of the eye can be created by combining several images of various eye-structures as image-portions.

In step 110 the eye can be positioned relative to the OCT imaging system. There are a large number of ways to position the eye, which include lowering a gantry onto the eye until a patient interface or a frontal segment of an objective makes mechanical contact with the eye. Some systems use a vacuum system to generate a gripping force between the patient interface and the eye and to effectively immobilize the eye relative to the imaging system. Others use mechanical means, such as a corrugated surface pressed gently into the cornea.

The imaging system can be an Optical Coherence Tomographic (OCT) imaging system. Embodiments of the method 100 typically utilize a Spectral Domain (SD) OCT technique, instead of the Time Domain OCT technology. The SD-OCT technique can be practiced by a Spectrometer Based OCT (SB-OCT) or a Swept Source OCT (SS-OCT) imaging system. It has been widely documented that Spectral Domain OCT techniques perform qualitatively faster and with higher precision than Time Domain OCT systems.

In step 120 the SD-OCT system can be used to create an image of the eye. If the SD-OCT is practiced without following the steps of method 100, it generates direct and mirror images of the imaged objects. As explained above, this proliferation of the images leads to an imaging ambiguity and thus undermines the utility of the OCT imaging system for ophthalmic or any other applications.

FIG. 2 illustrates the example of a the capsule 51 being imaged by SD-OCT, its two most prominent structural elements, the anterior capsule layer and the posterior capsule layer each generating a direct and mirror image, potentially leading to overlapping and ambiguous imaging of the capsule 51. Such ambiguity and the resulting loss of precision can confuse the surgeon and thus undermines the efficiency and precision of the cataract surgery, among others.

The method 100 will be primarily described in connection with the anterior and posterior capsule layers 51A-P as these layers have a high optical contrast and thus produce the most pronounced image in an OCT imaging process. However, the anterior lens surface 52A and the posterior lens surface 52P, as well as the anterior and posterior surfaces of the hard nucleus 53A-P are also visible in the OCT image, albeit with less contrast. Therefore, the problem of complex ambiguity also manifests itself by a direct or mirror image of the lens surfaces 52A-P or nucleus surfaces 53A-P overlapping with the direct or mirror images of the capsule layers 51A-P. These overlaps pose analogous problems as the direct and mirror images of the capsule layers overlapping each other and therefore will only be referred to without spelling out all the various combinations of the overlaps. This simplification is used only to preserve the conciseness of the description and the scope of the invention includes all possible overlap combinations of these imaged eye-structures.

To capture all these possible combinations, the method will be described in terms of a first eye-structure and second eye-structure. The above described anterior and posterior capsule layers 51A-P are examples for these eye-structures. Other eye-structures include the anterior and posterior lens surfaces 52A-P and the anterior and posterior nucleus surfaces 53A-P, as well as the iris, the pupil, the cornea, or any other eye-structures.

Further, it is noted that throughout this application the term "surface" is used in a broad sense: it can refer not only to a geometric outermost surface, but to a biological layer of some thickness. The thickness of a surface, or surface layer, can be defined based on functional, biological or mechanical criteria, and can extend from below a micron to above a millimeter. Also, the term "layer" can refer to not only to well separated layers with clearly defined boundaries, but carries a broader meaning, including layers defined by a boundary whose contrast relative to its neighbors is only moderate, as long as it still allows a distinction from its neighboring structures.

To eliminate the complex ambiguity, in steps 120-150 an image of the eye can be assembled by selecting only one of the mirror and direct images of the imaged eye-structures. In detail, in step 130 a first image-portion is generated which corresponds to either the direct image or the mirror image of a first eye structure, such as the anterior capsule layer. In step 140 a second image-portion is generated which corresponds to either a mirror or a direct image of a second eye-structure, such as the posterior capsule.

Then, in step 150, the non-selected images of the first and second eye-structures can be suppressed, allowing the assembly of an image from the generated first and second image-portions.

In the context of steps 120-140 it is noted that a reference depth of the imaging system is one of the control parameters which sets the depth, or Z coordinates, of the mirror images.

In other implementations other control parameters can play the role of the reference depth.

A component of the imaging step 120 can be adjusting this reference depth, or another analogous control parameter, of the SD-OCT imaging system to generate the direct and mirror images of the first and second eye-structures so that the images can be distinguished from each other. The reference depth can be adjusted e.g. by moving a reference mirror in a reference arm of the SD-OCT imaging system. In other implementations, a variable delay element can be employed in either the reference arm or in an imaging arm of the SD-OCT system.

This judicious choice of the reference depth makes the step of distinguishing between the direct and mirror images of the first and second eye-structures at least easier, and often in fact possible. Once the direct and mirror images of the first and second eye-structures are distinguished, it becomes possible to display only the selected images as the first and second image-portions of an image of the eye, and suppress the non-selected images. These steps are an efficient method to eliminate the complex ambiguity.

The distinguishing of the direct and mirror images of the first and second eye-structures can be performed by a variety of methods, including visually recognizing a spatial separation of the images, or applying a pattern recognition approach, or distinguishing a signal or noise characteristic of the images, or utilizing pre-existing knowledge about the eye, or utilizing knowledge about the eye based on a diagnostic process.

These image distinguishing methods can be combined iteratively with the step of adjusting the reference depth. In some implementations, the distinguishing of the images step can be attempted using a specific reference depth, such as a preset or default depth. If the images can be distinguished with a high confidence level, then no adjustment of the reference depth is required. However, if the attempt to distinguish the image-portions does not succeed, or does not reach a desired confidence level, then the reference depth can be adjusted and the distinguishing step can be performed again. These steps can be practiced iteratively until the reference depth is adjusted to a level where a high confidence level distinction of the image-portions is achieved.

Once the reference depth is chosen so that the direct and mirror images of the first and second eye-structures are distinguishable, the non-selected images can be suppressed in step 150 in a variety of ways, including preventing the display of the generated non-selected images, generating the non-selected images without displaying the non-selected images, and performing a computational step to prevent even the generation of the non-selected images. Other software and hardware implementations can also suppress the non-selected images as well.

In sum, the method 100 of distinguishing various eye-structure images, selecting some of the distinguished images and suppressing the non-selected images in some implementations includes (a) attempting to distinguish the direct and mirror images of one or more eye-structures; (b) tuning a control parameter, such as the reference depth, if necessary, in response to the attempted distinguishing step to improve the efficiency of the distinguishing step (a); and (c) possibly performing steps (a) and (b) in an iterative manner to optimize the outcome of the distinguishing step.

In the case of an imaging process with 2×2=4 images (direct and mirror images of two main eye-structures), this distinguishing step enables the imaging system to suppress two non-selected images and use the two selected images as image-portions to assemble an accurate and useful image of the surgical region of the lens which is free of the complex ambiguity.

Assembling the eventually displayed image may include performing a transformation on one of the first and second image-portions to generate a biologically representative image of the first and second eye-structures in step 150, when at least one of the first and the second image-portions is a mirror image. This transformation can be e.g. a mirroring of the mirror image relative to a suitably chosen mirror plane or line, thus creating a direct image. Such a transformation may not be necessary when the first and the second image-portions are direct images.

Figure 3B:
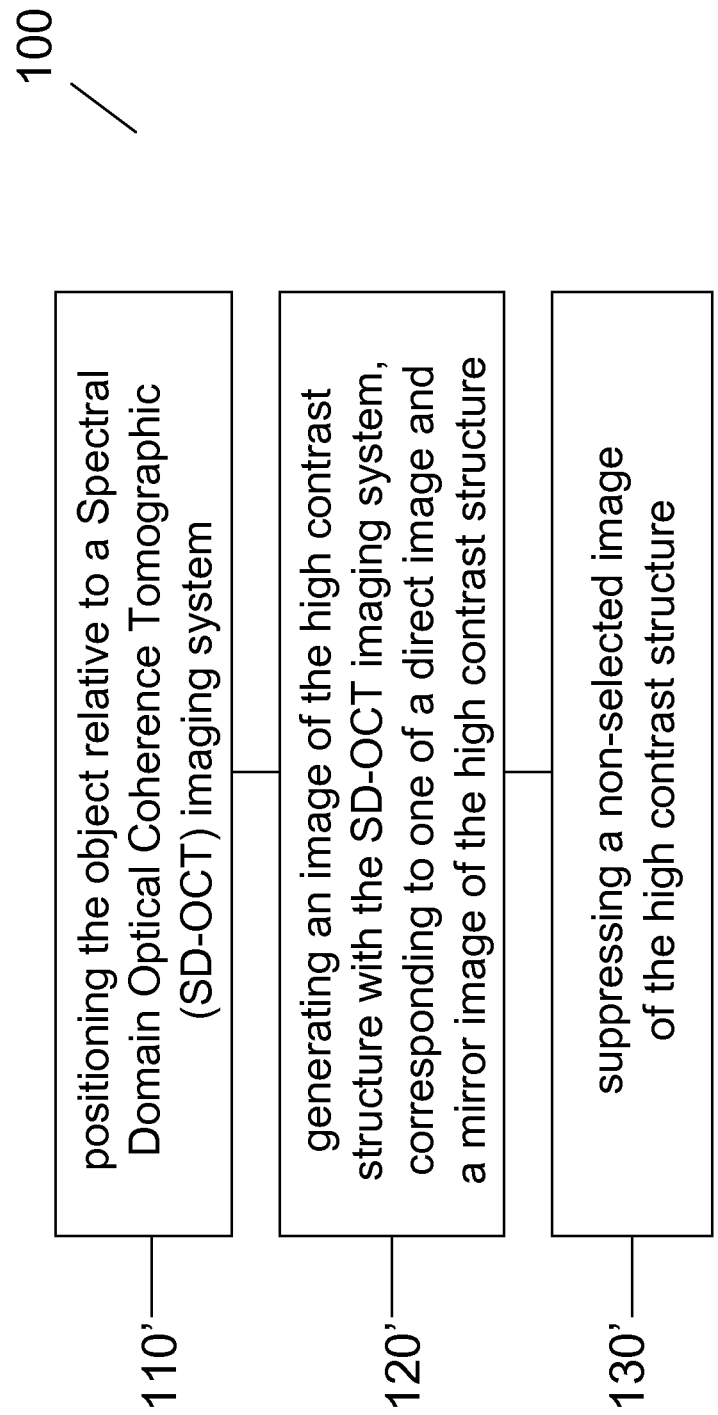
FIG. 3B illustrates the steps of an exemplary imaging method.

FIG. 3B illustrates a related method of imaging 100'. The method 100' can include the steps of:

(110')—positioning an object relative to a Spectral Domain Optical Coherence Tomographic (SD-OCT) imaging system, the object including a high contrast structure in a low contrast medium;

(120')—generating an image of the high contrast structure with the SD-OCT imaging system, corresponding to one of a direct image and a mirror image of the high contrast structure; and (130')—suppressing a non-selected image of the high contrast structure.

The method 100' focuses on distinguishing the direct image and the mirror image of the high contrast object in step 120', as well as on distinguishing either of these images from another image of interest. The method also displays one of these images, suppressing the other, non-selected image. The method 100' can distinguish between the mirror image, the direct image and any other image e.g. by adjusting a reference depth of the SD-OCT imaging system to generate the image of the high contrast structure at a suitable image depth so that the image of the high contrast structure is distinguishable from a first image of a first structure.

As above, the distinguishing step can include visually recognizing a spatial separation of the image of the high contrast structure from the first image; applying a pattern recognition approach; distinguishing a signal characteristic of the image of the high contrast structure and the first image; and utilizing pre-existing knowledge about the object; and utilizing a knowledge about the object based on a diagnostics.

Finally, the steps of adjusting the reference depth and the distinguishing the various images can be performed iteratively for optimized performance.

FIGS. 4A-D illustrate that, when the eye is imaged by an SD-OCT procedure with its thin cornea and the anterior and posterior capsule layers, several different image sequences can arise depending on the choice of the reference depth Zref. As noted above, in addition to the capsule layers, the lens surface and the nucleus surface also appears in an OCT image. Thus, while below the image sequences are discussed only in terms of the capsule layers, the various combinations of the locations of the additional images generate several additional sequences. Since these additional image sequences do not raise qualitatively new issues, practicing the natural extensions of the method 100 is sufficient to eliminate the corresponding complex ambiguity.

Figure 4A:
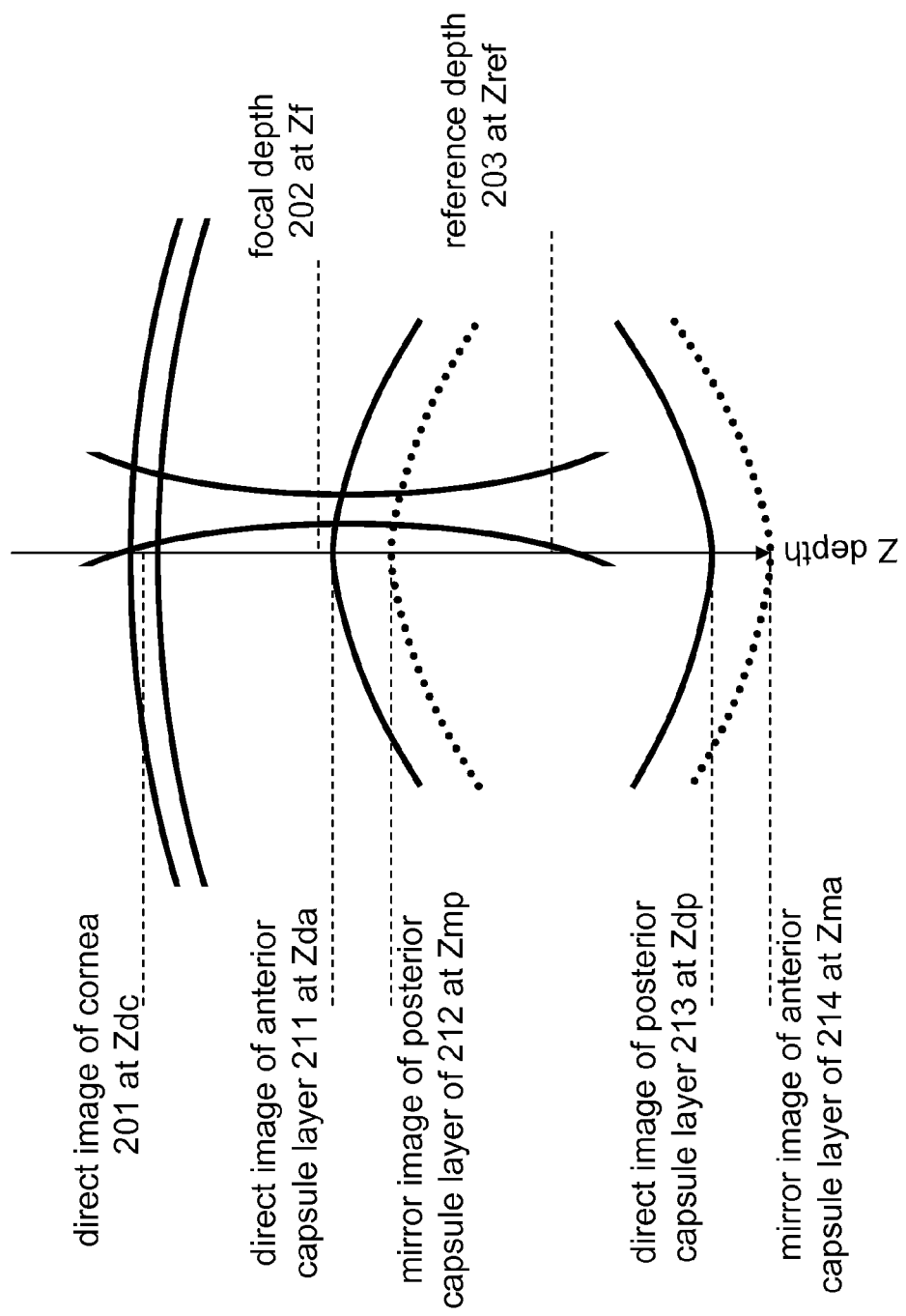
FIGS. 4A-F illustrate examples of image-portion sequences.

As shown in FIG. 4A, the depth Zdc ($=Z_{direct, cornea}$) of the direct image 201 of the cornea can be used as a zero of the Z depth scale. Then the direct image 211 of the anterior capsule layer can be at a depth Zda and the direct image 213 of the posterior capsule layer at a depth Zdp.

FIG. 4A also illustrates that for a particular depth choice Zref of the reference depth 203, the SD-OCT imaging system can generate the mirror images of surfaces with the reference depth Zref as the center of reflection. In general, a Z depth of a mirror image is located at Zmirror=Zref−(Zmirror31 Zref).

The mirror images of the above surfaces and their depths are then as follows: a mirror image 212 of the posterior capsule layer at depth Zmp and a mirror image 214 of the anterior capsule layer at depth Zma, so that the sequence of image depths is: Zdc-Zda-Zmp-Zdp-Zma.

Figure 4B:
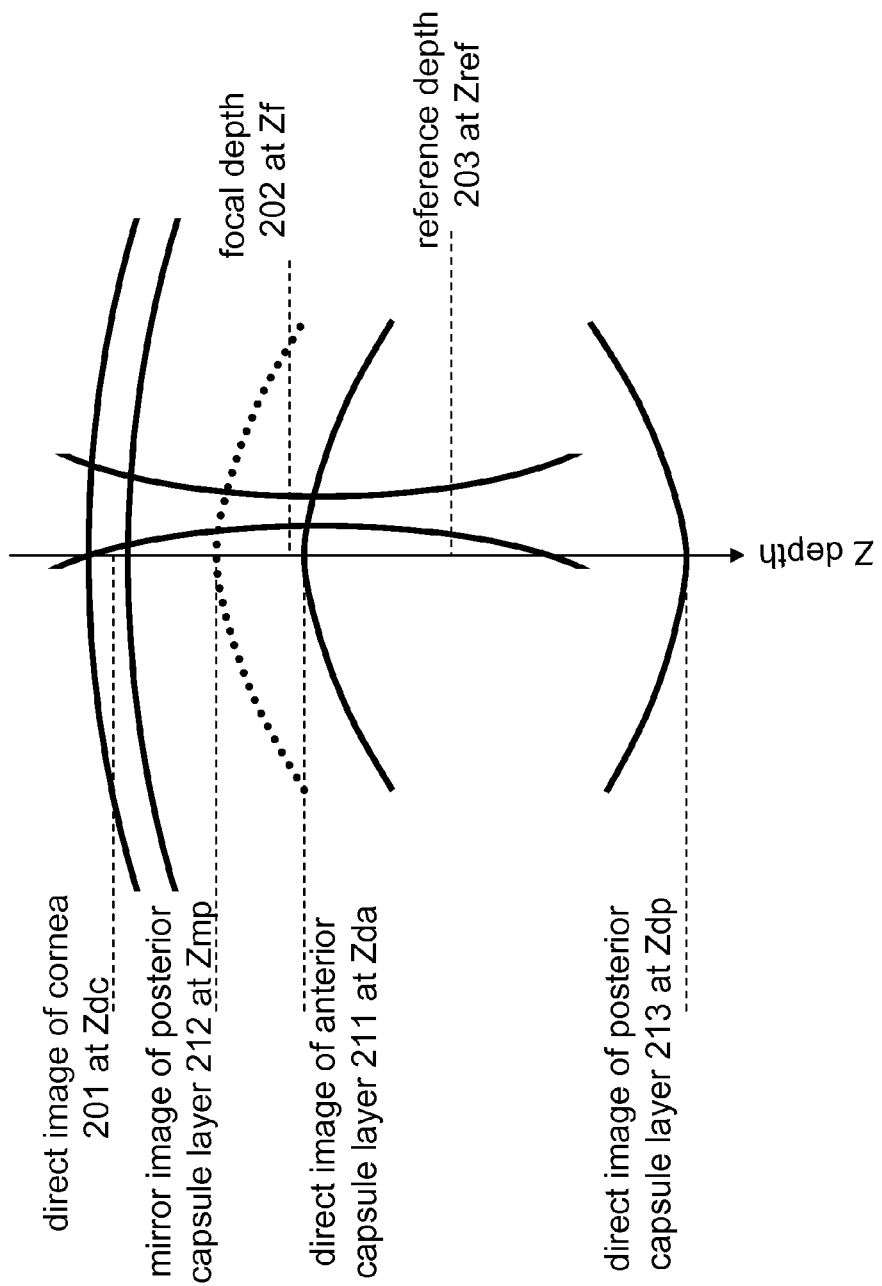
Figure 4C:
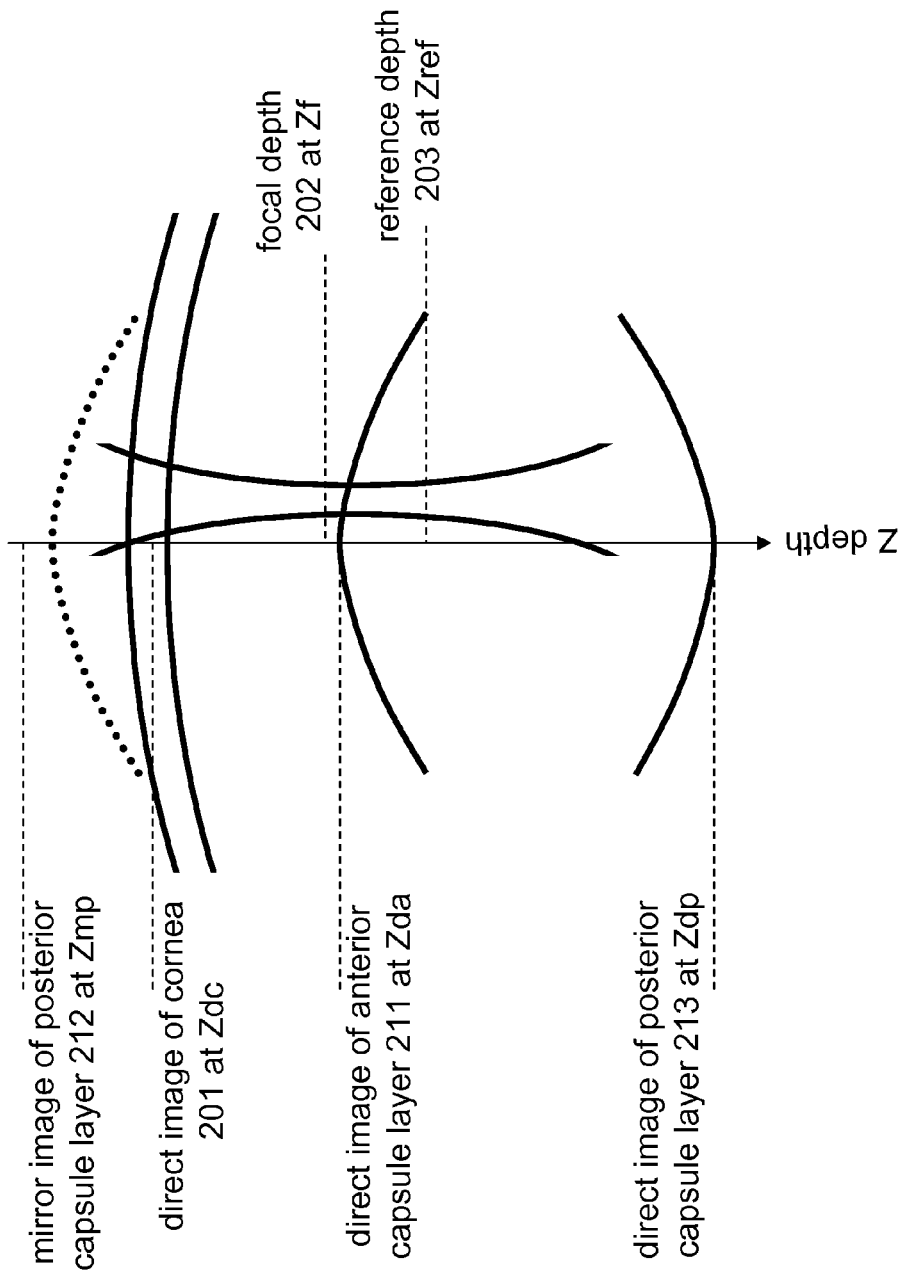

FIGS. 4B-C illustrate that as the Z coordinate Zref of the reference depth 203 is tuned, the image sequences can change. Since in the practically relevant cases typically the mirror image of the anterior capsule layer 214 has the deepest Z depth at Zma, followed by the Z depth of the direct image of the posterior capsule layer at Zdp, these two will not be explicitly stated to simplify the discussion. Thus, the description concentrates on the Z depth Zmp of the mirror image of the posterior capsule layer 212 relative to the other image depths Zdc and Zda.

With this simplification, the typical image depth sequences include:

FIG. 4A: Zdc-Zda-Zmp, i.e.: direct image of the cornea 201—direct image of the anterior capsule layer 211—mirror image of the posterior capsule layer 212;

FIG. 4B: Zdc-Zmp-Zda, i.e.: direct image of the cornea 201—mirror image of the posterior capsule layer 212—direct image of the anterior capsule layer 211; and FIG. 4C: Zmp-Zdc-Zda, i.e.: mirror image of the posterior capsule layer 212—direct image of the cornea 201—direct image of the anterior capsule layer 211.

Figure 4D:
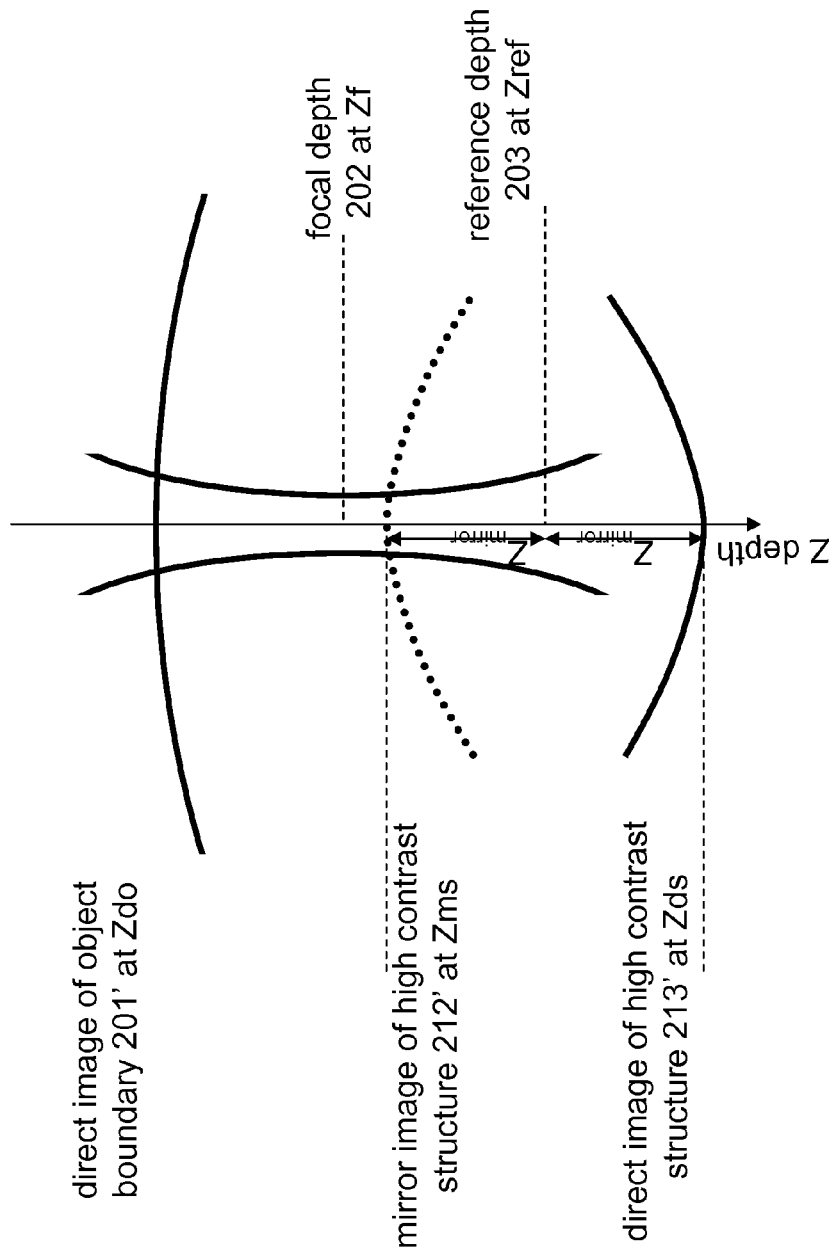

FIG. 4D illustrates an analogous image sequence for the related method 100': direct image of the object boundary 201'—mirror image of the high contrast object 212'—direct image of the high contrast object 213'.

In complementary embodiments the above sequences can take the exact complementary sequence, changing every direct image to a corresponding mirror image and every mirror image to the corresponding direct image.

To make connection to other terminologies in the literature, it is noted that the above descried imaging method is sometimes referred to as a homodyne imaging.

Figure 4E:
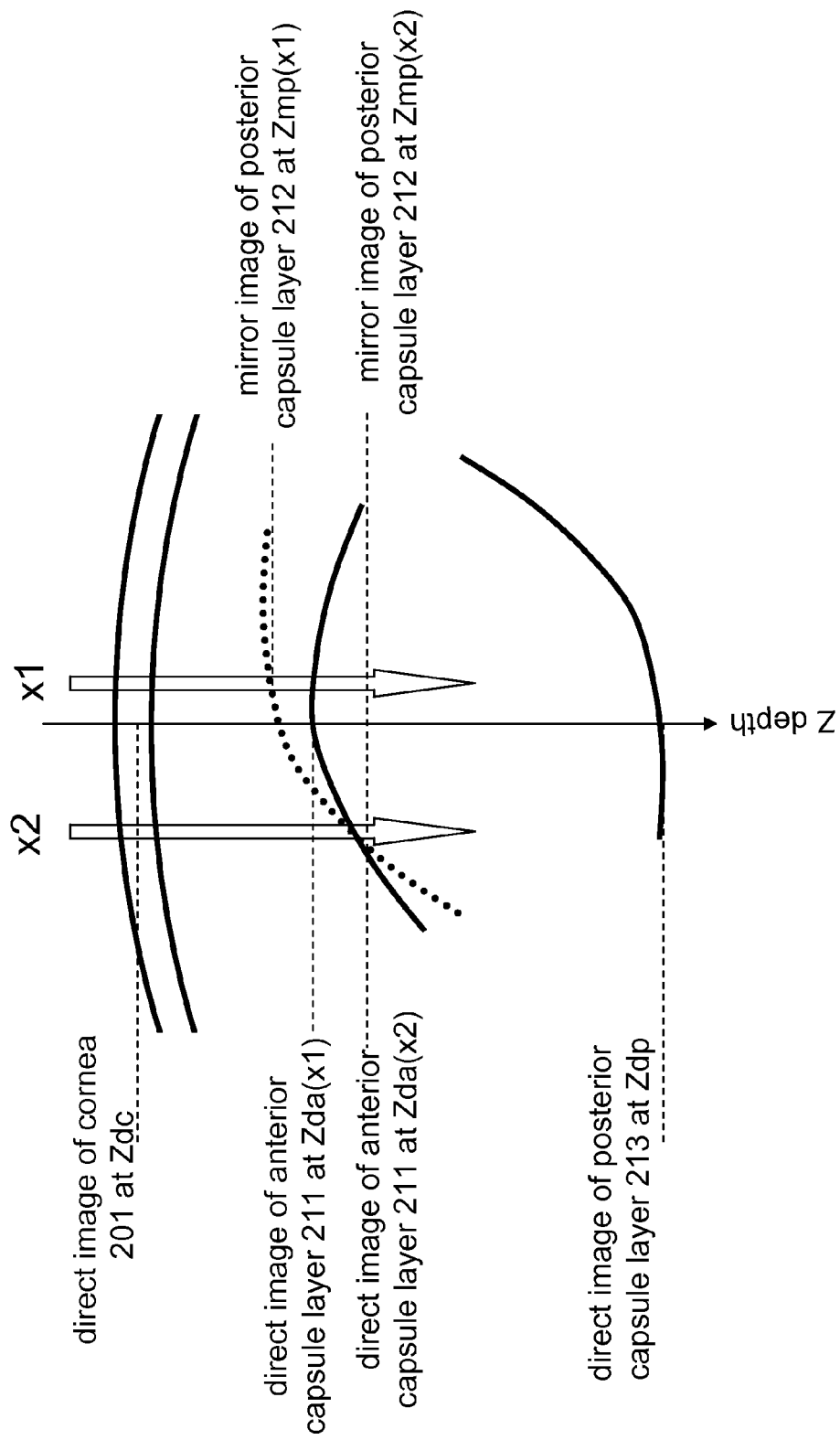
Figure 4F:
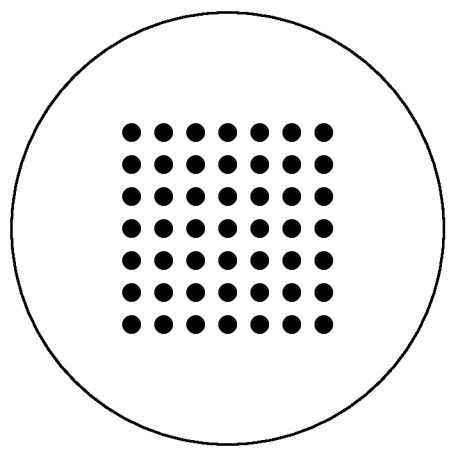
Figure 4F:
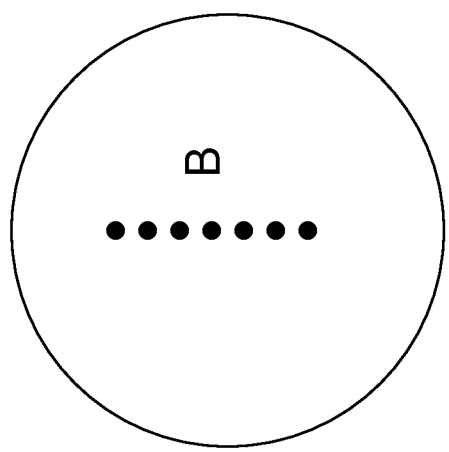
Figure 4F:
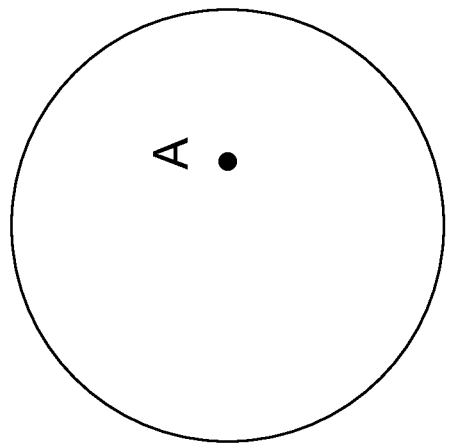

FIGS. 4E-F illustrate an implementation of method 100 which is related to the three dimensional nature of the imaged objects. In the previously described implementations the z-scanning is often performed along a single line: this approach is often referred to as an A-scan. However, an A-scan may provide incomplete information if the imaged object is not rotationally symmetric. This situation can occur e.g. if during an ophthalmic surgical procedure the lens is pushed into an asymmetrical position.

FIG. 4E illustrates such a situation when the center of the lens is shifted from the optical axis and it is tilted as well: its z axis ceases to be parallel with the optical axis. In this case, an A scan performed at an x1 planar location may find that the mirror image of the posterior capsule layer at the depth Zmp (x1) is distinguishable from the direct image of the anterior capsule layer Zda(x1). Here the x1 planar location vector can be expressed e.g. in Cartesian or radial coordinates.

However, if a more complete OCT image of the lens is desired e.g. to guide the ophthalmic surgery, then several Z-scans can be performed at planar locations x1, x2, . . . xn. As shown in FIG. 4E, if the A scan is performed at the x2 planar location then Zmp(x2) may be essentially equal to Zda(x2) and therefore the mirror image of the posterior capsule layer may be indistinguishable from the direct image of the anterior capsule layer.

FIG. 4F illustrates that a method 100" therefore may include a modified step 120" in which the eye, or any other imaged object, is imaged: along a single Z-scan ("A scan", left panel), (ii) in an imaging plane by a set of Z-scans ("B scan", center panel), or possibly in a circular B-scan, and (iii) in an imaging area by an x-y set of Z-scans (right panel).

Then in modified steps 130" and 140" one of a mirror or a direct image of the first and second eye-structures can be distinguished and selected. These steps may include adjusting method parameters, such as the reference depth Zref until the mirror and direct images do not overlap at any of the Z-scan locations and are thus distinguishable. Finally, in modified step 150" the non-selected images can be suppressed and the selected images displayed.

Figure 5A:
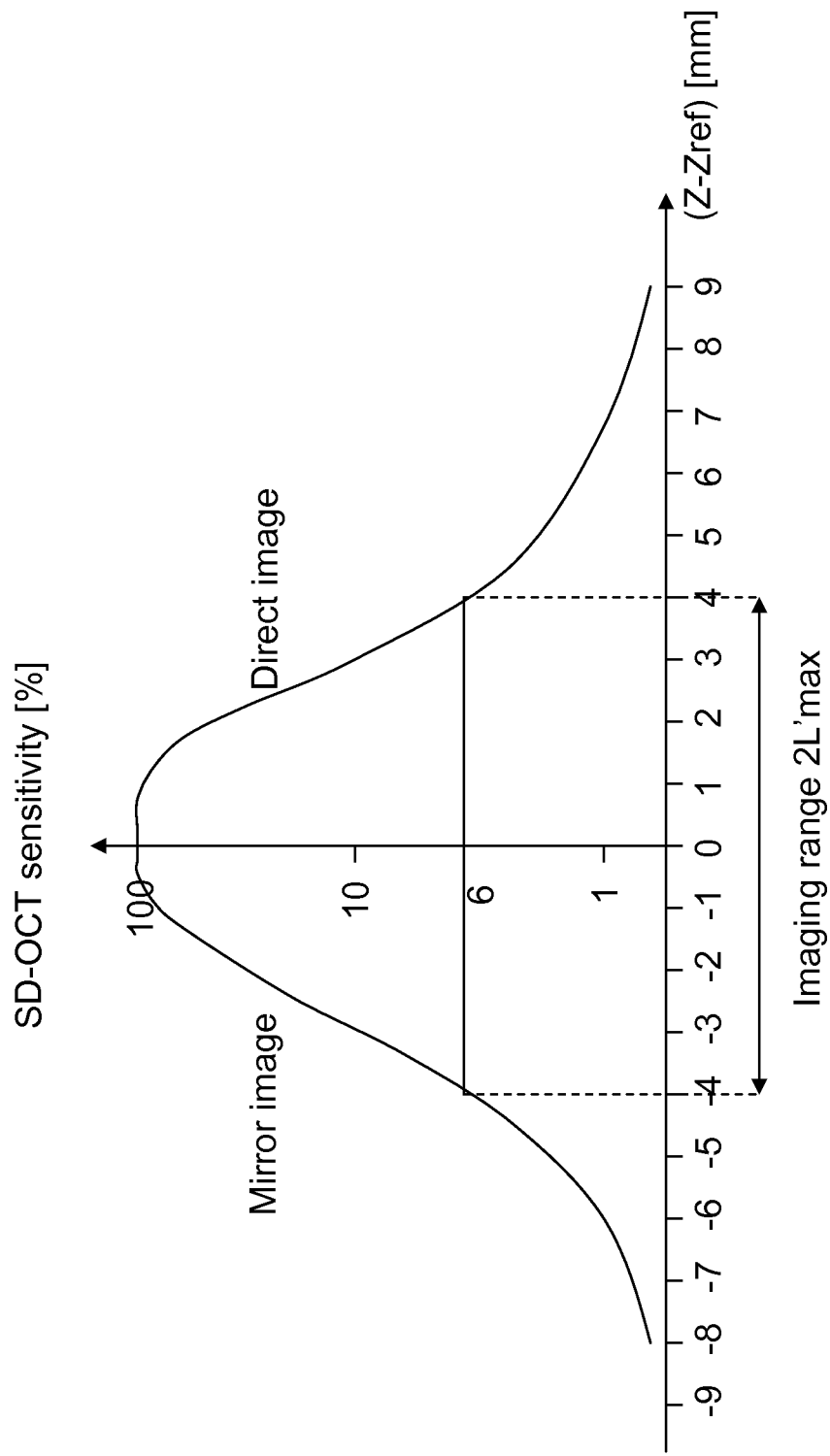
FIG. 5A illustrates the sensitivity of the SB-OCT system as a function of the imaging depth.

FIG. 5A illustrates how in a typical SD-OCT imaging system the sensitivity depends on the depth, or Z coordinate of the imaged object relative to the reference depth Zref. As shown, in some SD-OCT imaging systems as the Z coordinate of an object moves away from the reference depth Zref, the sensitivity can plummet fast. FIG. 5A illustrates that in some examples when the image Z coordinate departs from Zref by 4 millimeters, the sensitivity can decrease from a near 100% value to a value near 6%. When the (Z−Zref) is further increased to 6-7 millimeters, the sensitivity decrease from a near 100% value to a value around 1%. These values are only illustrative for specific examples. In general, the SD-OCT sensitivity can depend on (Z−Zref) according to a Gaussian, exponential or Lorentzian form.

This reduction of the sensitivity has numerous sources, including the finiteness of the coherence length of the applied light source, noise, the loss of signal strength, the difficulty of analyzing interference patterns at large path differences, and the various optical aberrations and astigmatisms. This loss of sensitivity is one of the key limiting factors of the range of applicability of the OCT imaging technique.

As shown in FIG. 5A, there are different ways to define an imaging range L'max of the SD-OCT system. A simple convention is to use the (Z−Zref) value where the sensitivity of the SD-OCT system is reduced below a threshold value, e.g. in the range of 5-10% of its maximum as half of the imaging range L'max: $L'max = |Z-Zref|_{(6\%)}$. Here the threshold value of 6% has been selected. Visibly, this definition does not depend on where the zero of the Z depth scale is set, as the SD-OCT sensitivity only depends on the difference of two Z depths. Other thresholds can be used as well.

To create high quality SD-OCT images of the targeted eye-structures, implementations of the methods 100 and 100' adjust the reference depth Zref and the imaging range L'max around the reference depth Zref so that the first and the second eye-structures of the method 100 or the high contrast object of the method 100' fall within an L'max/2 proximity of the reference depth Zref. The reference depth can be adjusted e.g. by moving a reference mirror in a reference arm of the SD-OCT imaging system. In other implementations, a variable delay element can be employed in either the reference arm or in an imaging arm of the SD-OCT system.

The imaging range L'max can be adjusted e.g. by adjusting at least one of a central wavelength and a wavelength resolution of the SD-OCT imaging system. These notions will be detailed when the SD-OCT system is described below.

To make the SD-OCT system suitable for cataract surgeries, some implementations of the methods 100 and 100' adjust the imaging range L'max to be in the 5-mm range. Implementations where cataract procedures are complemented with corneal procedures can have an imaging range L'max in the 0-15 mm range.

FIG. 5B illustrates some of the characteristics of the imaging laser beam. The imaging beam is typically expanded within the imaging laser system and then refocused at a focus depth Zf with a small numerical aperture NA and a narrow "beam-waist" at the focal depth Zf.

Around this beam waist, the notion of a Rayleigh range 220, or its double, a Z directional "depth of focus" can be introduced, where the beam is still narrow enough to image the object with high enough resolution. The formulaic expressions for these quantities will be given in the context of the system's description later. Here it is stated that implementations of the method can adjust this Rayleigh range around the focal depth Zf to result in the imaging range L'max to be less than 4 times the Rayleigh range. In other cases, this numerical factor can be different from four, e.g. in the range of 1-10.

Another length scale which can be adjusted is the reference depth Zref. In some implementations, e.g. cataract applications, the Zref reference depth 203 can be adjusted to be within the range of 2-15 mm. As discussed above, the reference depth can be adjusted e.g. by moving a reference mirror in a reference arm of the SD-OCT imaging system. In other implementations, a variable delay element can be employed in either the reference arm or in an imaging arm of the SD-OCT system.

Figure 6A:
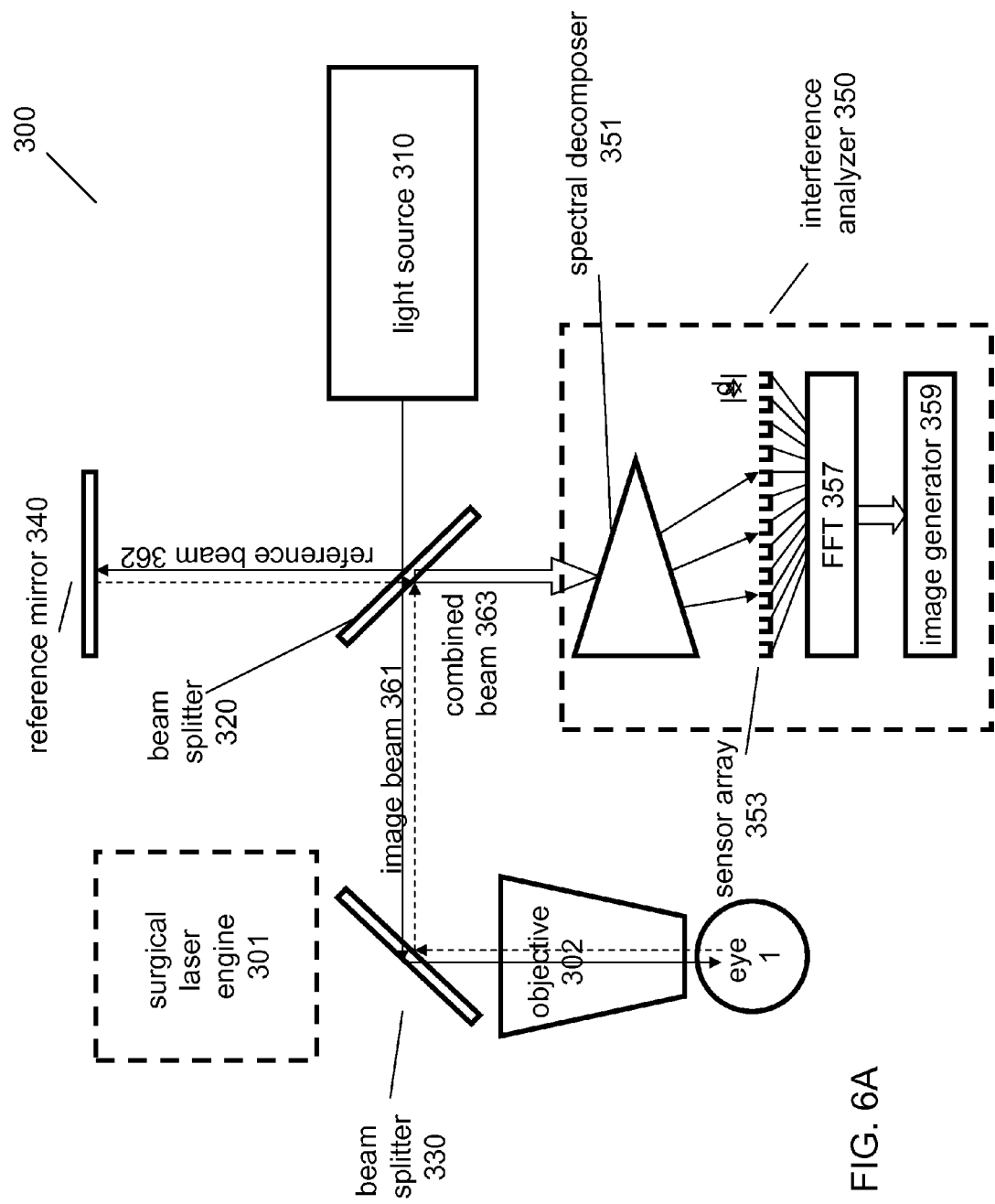
FIGS. 6A-B illustrate two examples of the OCT imaging system.
Figure 6B:
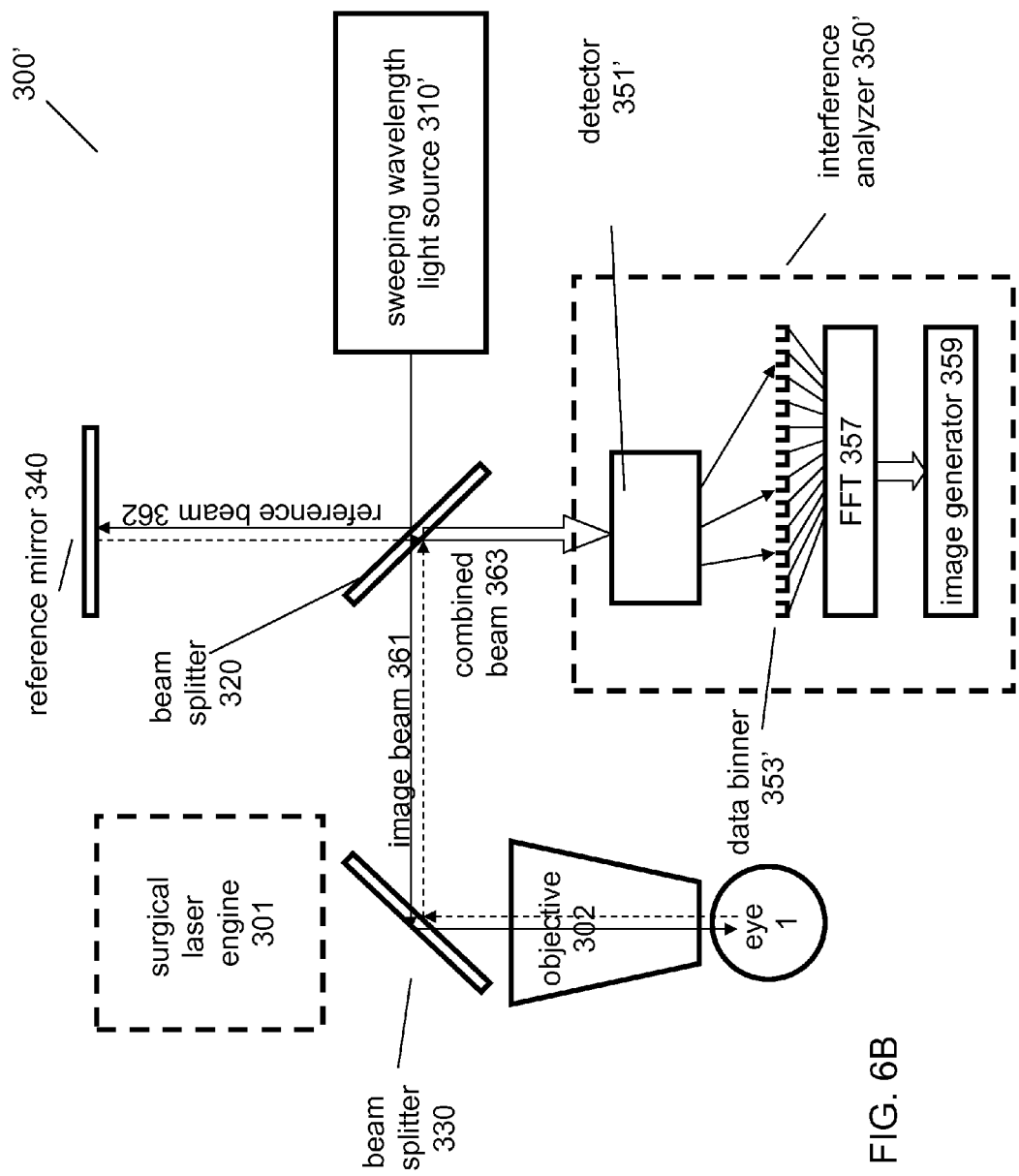

FIGS. 6A-B illustrate two embodiments of the SD-OCT imaging systems 300 and 300', on which methods 100 and 100' can be practiced.

FIG. 6A illustrates that the imaging system 300 can include a light source 310, which generates light with a mean wavelength $\lambda_0$ and a relatively broad finite bandwidth W. In some typical examples, $\lambda_0$ can be in the 800-1100 nm range, and W can be in the 10-50 nm range. The generated beam can reach a beam splitter 320, which splits the generated light beam into an image beam 361 and a reference beam 362. The image beam 361 continues towards a second beam splitter 330, which can redirect the image beam into the optics of the surgical beam (generated by a surgical laser engine 301). The last element of this shared beam path is typically an objective 302. The objective 302 can make direct or indirect contact with the imaged object, such as the eye 1, as described in the step 110 of the method 100. A function of this contact is to position and immobilize the eye relative to the objective 302 in order to allow for a high precision imaging and subsequent ophthalmic surgical procedure. In some cases a patient interface is attached to the end of the objective 302 to facilitate this contact efficiently using vacuum suction.

The dotted lines indicate the portion of the image beam returned from the imaged object such as the eye 1 or the high contrast object of method 100'. This returned portion of the image beam 361 backtracks its path and reaches the beam splitter 320 again.

The beam splitter 320 can redirect another portion of the light generated by the light source 310 as a reference beam 362 towards a reference mirror 340. The reference mirror 340 can return a portion of the reference beam towards the beam splitter 320. Here the broader term "return" is used instead of reflect, as both the imaged object 1 and the reference mirror 340 may return only a fraction of the light incident on them. This is especially true in embodiments which use a delay element in place of or in conjunction with the reference mirror 340.

The beam splitter 320 can recombine the returned image beam portions and reference beam portions into a combined, or interference beam 363. In some implementations, the beam splitting function and the beam recombining function of the beam splitter 320 can be performed by two different optic units, such as two beam splitters.

The imaging systems 300 and 300' can use the Michelson-Morley architecture, where the distance to the reference mirror 340 is tunable. Typically, maximal constructive interference is obtained between the reference beam 362 and that portion of the image beam 361 which traveled a path with the same optical length. Therefore, the distance of the reference mirror 340 to the beam splitter/combiner 320 is a key factor determining the Z coordinate Zref of the reference depth 203. Accordingly, adjusting the distance or the length of the optical pathway to the reference mirror 340 is one way to practice some steps of the method 100, such as tuning the Zref reference depth in the range of 2-15 mm. In general, the length of the optical pathway depends not only on the distance, but also on the index of refraction of the medium the light propagates in. In general, the distance to the reference mirror 340 can be tuned so that the reference beam 362 is returned with either a time delay or a time advance to the beam combiner 320.

In SD-OCT systems an additional feature is the use of a light source 310 with a finite bandwidth W. These systems can be thought of as many Michelson-Morley (MM) interferometers operating in parallel at different wavelengths. Since the MM systems operating at different wavelengths image the object 1 at different depth, the combined beam 363 carries the interference and thus the image information from all depths of the object 1.

To recover the image information for each depth, the combined beam 363 is decomposed into its different wavelengths components. The interference data of each wavelength component are analyzed in parallel to recover the image data corresponding to each depth. These image data is then used to construct an overall image. In effect, the interference data carried by the different wavelength components can be translated into a simultaneous or essentially instantaneous Z scanning of the imaged object. This translation of the interference data into Z-scanning data is carried out by an interference analyzer 350.

FIG. 6A illustrates that in some implementations of the OCT system 300 the interference analyzer 350 is a spectrometer based (SB) system. Using standard optical analysis, the critical imaging and performance parameters of the SB-OCT system 300 and SS-OCT system 300' can be characterized by the architectural and design parameters as follows.

The SB interference analyzer 350 can include a spectral decomposer 351, which can be a grating, prism or equivalent. It can decompose the combined or interfering beam 363 and send each light component in the narrow vicinity of a wavelength in a different direction with angle $\phi_i$.

The interference analyzer 350 can further include a sensor or pixel array 353 to detect these diverging beam components essentially simultaneously. Each pixel records the interference data carried by the $\lambda_i$ wavelength component of the combined beam 363 within a narrow $\delta\lambda$ wavelength range. These interference data are representative of the image data corresponding to a particular depth within the object 1. As a detailed analysis reveals, the image data representing the full Z-scan of the object can be reconstructed by performing a (fast) Fourier Transformation (FFT) on the interference data recorded by the pixels/sensors. The FFT can be performed by an FFT processor 357, sending its image data output to an image generator 359. The image generator 359 can generate the actual image from these image data representing a Z-scan and send its output to a display unit, assisting the ophthalmic surgeon.

The smaller and more densely packed the individual pixels, the narrower $\delta\lambda$ wavelength ranges they can resolve. The other quantity determining $\delta\lambda$ besides the pixel density is the total range of wavelengths, i.e. the "bandwidth W" of the imaging light source 310. In a simple arrangement, $\delta\lambda$ is proportional to the bandwidth W and inversely proportional to the number of pixels in a row of the sensor array 353. The narrower the δλ wavelength ranges, the broader the imaging range in the z direction because these two quantities are connected by an inverting Fourier transform. In particular, the theoretical maximum imaging range is given by $$L\max = \frac{1}{4}\left(\frac{\lambda_0^2}{\delta\lambda}\right) = \frac{1}{2}\frac{1}{Nf} \quad (1)$$

The value $\lambda_0$ refers to the average or central wavelength of the OCT light source 310 and Nf denotes the Nyquist frequency. This Lmax is a theoretical limit of the imaging range. In reality, additional factors may limit the effective imaging range below this theoretical maximum, such as the signal to noise ratio. Therefore the imaging range L'max, introduced earlier, is typically smaller than or equal to this theoretical value Lmax.

Δz, the resolution in the z direction, also known as the "axial resolution" is given by:

$$\Delta z = \frac{2\ln 2}{\pi}\left(\frac{\lambda_0^2}{W}\right) \quad (2)$$

Δx, the resolution in the x direction, or "transverse resolution" is governed by the numerical aperture NA and the wavelength of the imaging light source 310, and can be expressed as:

$$\Delta x = \frac{4}{\pi}\left(\lambda_0 \frac{f}{d}\right) \quad (3)$$

where f is the focal length and d is the pupil of the objective 302.

Finally, the above discussed Rayleigh range, is given by:

$$R = \frac{\pi}{2}\left(\frac{(\Delta x)^2}{\lambda_0}\right) \quad (4)$$

The Rayleigh range R is often defined as the z directional distance between the focal depth and the depth where the beam's width is $\sqrt{2}$ times the width at the focal depth. Thus, R characterizes the z-range within which the beam is narrow enough to enable high resolution imaging as limited by geometrical and wave optics. Lmax can be thought of as characterizing the z-imaging range as limited by the light source 310 and the resolution of the sensor array 353. A system design principle often thought of as optimal, e.g. for Gaussian beams, is to make these two z-ranges align with each other. For example, in some implementations, Lmax=4R. The same design principle can be captured by the "depth of focus", which is often defined as twice the Rayleigh range.

The above formulas express the method parameters, including Lmax, Zref and R in terms of the architectural or system parameters including λ, δλ, W, f and d, and thus map out specific ways for adjusting the method parameters by adjusting the system parameters.

For example, Eq. (1) indicates that the imaging range Lmax method parameter can be adjusted by adjusting the central wavelength $\lambda_0$ of the OCT light source 310 and/or the wavelength resolution δλ of the sensor array 353. Further, the reference depth Zref method parameter can be adjusted by changing the distance to the reference mirror 340 system parameter or by placing a variable delay element into the path of the reference beam 362. Alternatively, the path of the image beam 361 can be modified as well, e.g. by changing the distance between the beam splitters 320 and 330, or by placing a variable delay element between them.

FIG. 6B illustrates another embodiment of the OCT system 300'. This embodiment 300' uses a so-called "swept source" (SS) light source, or sweeping wavelength light source 310'. Such SS light sources 310' emit coherent light with a much narrower bandwidth than the spectrometer based SB light source 310. By clever modulation techniques the SS light sources 310' vary the wavelength of the emitted light, "sweeping" the wavelength 2 across a bandwidth W. Therefore, in such SS-OCT systems 300' the Z-scanned image data is captured not spatially but as a time sequence as the wavelength λ is swept. In such SS-OCT systems 300' the actual Z-scanned image can be generated by performing a Fast Fourier Transform on the spectrum of the combined beam 363.

To carry out this functionality, the interference analyzer 350' of the SS-OCT systems 300' can utilize a detector 351' to receive the combined or interfering beam 363, which can be synchronized with the sweeping light source 310'. The detector 351' can bin the incoming sequence of interference data into a data binner 353' according to what wavelength light the light source 310' was emitting in the corresponding short time interval. Since resolving the time sequence in SS-OCT systems is in some sense analogous to resolving the wavelength composition of the combined beam in the SB-OCT systems, the rest of the interference analyzer 350' can be analogous to the SB-OCT system 300. Thus, the SS-OCT interference analyzer 350' also includes a Fast Fourier Transform (FFT) processor 357, which now Fourier transforms the spectrum of the time sequence of the interference data to generate the image data and sends its output to an image generator 359, which assembles the Z-swept image of the imaged object, such as the eye 1.

A function of the image generator 359 in either architecture is to contribute to the process of distinguishing the direct and mirror images of the first and second eye-structures. In some implementations, a separate processor is working together with the image generator 359 to achieve this goal. As discussed above, this distinguishing step can involve e.g. visually recognizing a spatial separation of the image of the high contrast structure from the first image, applying a pattern recognition approach, distinguishing a signal characteristic of the image of the high contrast structure and the first image, and utilizing pre-existing knowledge about the object; and utilizing a knowledge about the object based on a diagnostics.

Furthermore, the image generator 359 and the extra image processor can suppress the non-selected images by e.g. preventing the display of generated non-selected images, generating the non-selected images without displaying the non-selected images, and performing a computational step to prevent the generation of the non-selected images.

FIGS. 7-17 illustrate embodiments of an ophthalmic laser surgery system which employ an SD-OCT imaging subsystem.

One important aspect of laser surgical procedures is precise control and aiming of a laser beam, e.g., the beam position and beam focusing. Laser surgery systems can be designed to include laser control and aiming tools to precisely target laser pulses to a particular target inside the tissue. In various nanosecond photodisruptive laser surgical systems, such as the Nd:YAG laser systems, the required level of targeting precision is relatively low. This is in part because the laser energy used is relatively high and thus the affected tissue area is also relatively large, often covering an impacted area with a dimension in the hundreds of microns. The time between laser pulses in such systems tend to be long and manual controlled targeting is feasible and is commonly used. One example of such manual targeting mechanisms is a biomicroscope to visualize the target tissue in combination with a secondary laser source used as an aiming beam. The surgeon manually moves the focus of a laser focusing lens, usually with a joystick control, which is parfocal (with or without an offset) with their image through the microscope, so that the surgical beam or aiming beam is in best focus on the intended target.

Such techniques designed for use with low repetition rate laser surgical systems may be difficult to use with high repetition rate lasers operating at thousands of shots per second and relatively low energy per pulse. In surgical operations with high repetition rate lasers, much higher precision may be required due to the small effects of each single laser pulse and much higher positioning speed may be required due to the need to deliver thousands of pulses to new treatment areas very quickly.

Examples of high repetition rate pulsed lasers for laser surgical systems include pulsed lasers at a pulse repetition rate of thousands of shots per second or higher with relatively low energy per pulse. Such lasers use relatively low energy per pulse to localize the tissue effect caused by laser-induced photodisruption, e.g., the impacted tissue area by photodisruption on the order of microns or tens of microns. This localized tissue effect can improve the precision of the laser surgery and can be desirable in certain surgical procedures such as laser eye surgery. In one example of such surgery, placement of many hundred, thousands or millions of contiguous, nearly contiguous or pulses separated by known distances, can be used to achieve certain desired surgical effects, such as tissue incisions, separations or fragmentation.

Various surgical procedures using high repetition rate photodisruptive laser surgical systems with shorter laser pulse durations may require high precision in positioning each pulse in the target tissue under surgery both in an absolute position with respect to a target location on the target tissue and a relative position with respect to preceding pulses. For example, in some cases, laser pulses may be required to be delivered next to each other with an accuracy of a few microns within the time between pulses, which can be on the order of microseconds. Because the time between two sequential pulses is short and the precision requirement for the pulse alignment is high, manual targeting as used in low repetition rate pulsed laser systems may be no longer adequate or feasible.

One technique to facilitate and control precise, high speed positioning requirement for delivery of laser pulses into the tissue is attaching a applanation plate made of a transparent material such as a glass with a predefined contact surface to the tissue so that the contact surface of the applanation plate forms a well-defined optical interface with the tissue. This well-defined interface can facilitate transmission and focusing of laser light into the tissue to control or reduce optical aberrations or variations (such as due to specific eye optical properties or changes that occur with surface drying) that are most critical at the air-tissue interface, which in the eye is at the anterior surface of the cornea. Contact lenses can be designed for various applications and targets inside the eye and other tissues, including ones that are disposable or reusable. The contact glass or applanation plate on the surface of the target tissue can be used as a reference plate relative to which laser pulses are focused through the adjustment of focusing elements within the laser delivery system. This use of a contact glass or applanation plate provides better control of the optical qualities of the tissue surface and thus allow laser pulses to be accurately placed at a high speed at a desired location (interaction point) in the target tissue relative to the applanation reference plate with little optical distortion of the laser pulses.

One way for implementing an applanation plate on an eye is to use the applanation plate to provide a positional reference for delivering the laser pulses into a target tissue in the eye. This use of the applanation plate as a positional reference can be based on the known desired location of laser pulse focus in the target with sufficient accuracy prior to firing the laser pulses and that the relative positions of the reference plate and the individual internal tissue target must remain constant during laser firing. In addition, this method can require the focusing of the laser pulse to the desired location to be predictable and repeatable between eyes or in different regions within the same eye. In practical systems, it can be difficult to use the applanation plate as a positional reference to precisely localize laser pulses intraocularly because the above conditions may not be met in practical systems.

For example, if the crystalline lens is the surgical target, the precise distance from the reference plate on the surface of the eye to the target tends to vary due to the presence of collapsible structures, such as the cornea itself, the anterior chamber, and the iris. Not only is their considerable variability in the distance between the applanated cornea and the lens between individual eyes, but there can also be variation within the same eye depending on the specific surgical and applanation technique used by the surgeon. In addition, there can be movement of the targeted lens tissue relative to the applanated surface during the firing of the thousands of laser pulses required for achieving the surgical effect, further complicating the accurate delivery of pulses. In addition, structure within the eye may move due to the build-up of photodisruptive byproducts, such as cavitation bubbles. For example, laser pulses delivered to the crystalline lens can cause the lens capsule to bulge forward, requiring adjustment to target this tissue for subsequent placement of laser pulses. Furthermore, it can be difficult to use computer models and simulations to predict, with sufficient accuracy, the actual location of target tissues after the applanation plate is removed and to adjust placement of laser pulses to achieve the desired localization without applanation in part because of the highly variable nature of applanation effects, which can depend on factors particular to the individual cornea or eye, and the specific surgical and applanation technique used by a surgeon.

In addition to the physical effects of applanation that disproportionably affect the localization of internal tissue structures, in some surgical processes, it may be desirable for a targeting system to anticipate or account for nonlinear characteristics of photodisruption which can occur when using short pulse duration lasers. Photodisruption is a nonlinear optical process in the tissue material and can cause complications in beam alignment and beam targeting. For example, one of the nonlinear optical effects in the tissue material when interacting with laser pulses during the photodisruption is that the refractive index of the tissue material experienced by the laser pulses is no longer a constant but varies with the intensity of the light. Because the intensity of the light in the laser pulses varies spatially within the pulsed laser beam, along and across the propagation direction of the pulsed laser beam, the refractive index of the tissue material also varies spatially. One consequence of this nonlinear refractive index is self-focusing or self-defocusing in the tissue material that changes the actual focus of and shifts the position of the focus of the pulsed laser beam inside the tissue. Therefore, a precise alignment of the pulsed laser beam to each target tissue position in the target tissue may also need to account for the nonlinear optical effects of the tissue material on the laser beam. In addition, it may be necessary to adjust the energy in each pulse to deliver the same physical effect in different regions of the target due to different physical characteristics, such as hardness, or due to optical considerations such as absorption or scattering of laser pulse light traveling to a particular region. In such cases, the differences in non-linear focusing effects between pulses of different energy values can also affect the laser alignment and laser targeting of the surgical pulses.

Thus, in surgical procedures in which non superficial structures are targeted, the use of a superficial applanation plate based on a positional reference provided by the applanation plate may be insufficient to achieve precise laser pulse localization in internal tissue targets. The use of the applanation plate as the reference for guiding laser delivery may require measurements of the thickness and plate position of the applanation plate with high accuracy because the deviation from nominal is directly translated into a depth precision error. High precision applanation lenses can be costly, especially for single use disposable applanation plates.

The techniques, apparatus and systems described in this document can be implemented in ways that provide a targeting mechanism to deliver short laser pulses through an applanation plate to a desired localization inside the eye with precision and at a high speed without requiring the known desired location of laser pulse focus in the target with sufficient accuracy prior to firing the laser pulses and without requiring that the relative positions of the reference plate and the individual internal tissue target remain constant during laser firing. As such, the present techniques, apparatus and systems can be used for various surgical procedures where physical conditions of the target tissue under surgery tend to vary and are difficult to control and the dimension of the applanation lens tends to vary from one lens to another. The present techniques, apparatus and systems may also be used for other surgical targets where distortion or movement of the surgical target relative to the surface of the structure is present or non-linear optical effects make precise targeting problematic. Examples for such surgical targets different from the eye include the heart, deeper tissue in the skin and others.

The present techniques, apparatus and systems can be implemented in ways that maintain the benefits provided by an applanation plate, including, for example, control of the surface shape and hydration, as well as reductions in optical distortion, while providing for the precise localization of photodisruption to internal structures of the applanated surface. This can be accomplished through the use of an integrated imaging device to localize the target tissue relative to the focusing optics of the delivery system. The exact type of imaging device and method can vary and may depend on the specific nature of the target and the required level of precision.

An applanation lens may be implemented with another mechanism to fix the eye to prevent translational and rotational movement of the eye. Examples of such fixation devices include the use of a suction ring. Such fixation mechanism can also lead to unwanted distortion or movement of the surgical target. The present techniques, apparatus and systems can be implemented to provide, for high repetition rate laser surgical systems that utilize an applanation plate and/or fixation means for non-superficial surgical targets, a targeting mechanism to provide intraoperative imaging to monitor such distortion and movement of the surgical target.

Specific examples of laser surgical techniques, apparatus and systems are described below to use an optical imaging module to capture images of a target tissue to obtain positioning information of the target tissue, e.g., before and during a surgical procedure. Such obtained positioning information can be used to control the positioning and focusing of the surgical laser beam in the target tissue to provide accurate control of the placement of the surgical laser pulses in high repetition rate laser systems. In one implementation, during a surgical procedure, the images obtained by the optical imaging module can be used to dynamically control the position and focus of the surgical laser beam. In addition, lower energy and shot laser pulses tend to be sensitive to optical distortions, such a laser surgical system can implement an applanation plate with a flat or curved interface attaching to the target tissue to provide a controlled and stable optical interface between the target tissue and the surgical laser system and to mitigate and control optical aberrations at the tissue surface.

Figure 7:
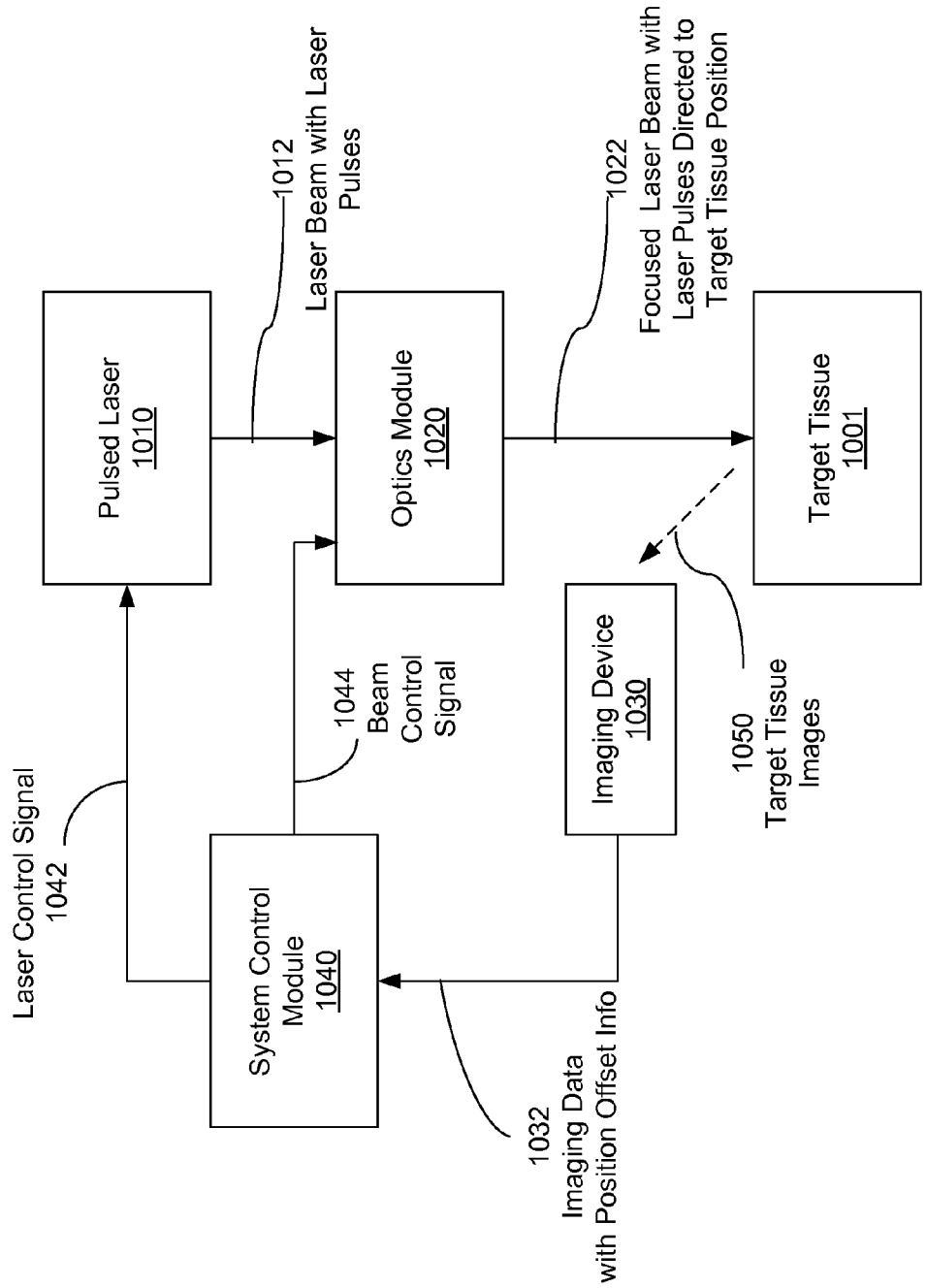
FIG. 7 shows an example of an imaging-guided laser surgical system in which an imaging module is provided to provide imaging of a target to the laser control.

As an example, FIG. 7 shows a laser surgical system based on optical imaging and applanation. This system includes a pulsed laser 1010 to produce a surgical laser beam 1012 of laser pulses, and an optics module 1020 to receive the surgical laser beam 1012 and to focus and direct the focused surgical laser beam 1022 onto a target tissue 1001, such as an eye, to cause photodisruption in the target tissue 1001. An applanation plate can be provided to be in contact with the target tissue 1001 to produce an interface for transmitting laser pulses to the target tissue 1001 and light coming from the target tissue 1001 through the interface. Notably, an optical imaging device 1030 is provided to capture light 1050 carrying target tissue images 1050 or imaging information from the target tissue 1001 to create an image of the target tissue 1001. The imaging signal 1032 from the imaging device 1030 is sent to a system control module 1040. The system control module 1040 operates to process the captured images from the image device 1030 and to control the optics module 1020 to adjust the position and focus of the surgical laser beam 1022 at the target tissue 1001 based on information from the captured images. The optics module 1020 can include one or more lenses and may further include one or more reflectors. A control actuator can be included in the optics module 1020 to adjust the focusing and the beam direction in response to a beam control signal 1044 from the system control module 1040. The control module 1040 can also control the pulsed laser 1010 via a laser control signal 1042.

The optical imaging device 1030 may be implemented to produce an optical imaging beam that is separate from the surgical laser beam 1022 to probe the target tissue 1001 and the returned light of the optical imaging beam is captured by the optical imaging device 1030 to obtain the images of the target tissue 1001. One example of such an optical imaging device 1030 is an optical coherence tomography (OCT) imaging module which uses two imaging beams, one probe beam directed to the target tissue 1001 thought the applanation plate and another reference beam in a reference optical path, to optically interfere with each other to obtain images of the target tissue 1001. In other implementations, the optical imaging device 1030 can use scattered or reflected light from the target tissue 1001 to capture images without sending a designated optical imaging beam to the target tissue 1001. For example, the imaging device 1030 can be a sensing array of sensing elements such as CCD or CMS sensors. For example, the images of photodisruption byproduct produced by the surgical laser beam 1022 may be captured by the optical imaging device 1030 for controlling the focusing and positioning of the surgical laser beam 1022. When the optical imaging device 1030 is designed to guide surgical laser beam alignment using the image of the photodisruption byproduct, the optical imaging device 1030 captures images of the photodisruption byproduct such as the laser-induced bubbles or cavities. The imaging device 1030 may also be an ultrasound imaging device to capture images based on acoustic images.

The system control module 1040 processes image data from the imaging device 1030 that includes the position offset information for the photodisruption byproduct from the target tissue position in the target tissue 1001. Based on the information obtained from the image, the beam control signal 1044 is generated to control the optics module 1020 which adjusts the laser beam 1022. A digital processing unit can be included in the system control module 1040 to perform various data processing for the laser alignment.

The above techniques and systems can be used deliver high repetition rate laser pulses to subsurface targets with a precision required for contiguous pulse placement, as needed for cutting or volume disruption applications. This can be accomplished with or without the use of a reference source on the surface of the target and can take into account movement of the target following applanation or during placement of laser pulses.

The applanation plate in the present systems is provided to facilitate and control precise, high speed positioning requirement for delivery of laser pulses into the tissue. Such an applanation plate can be made of a transparent material such as a glass with a predefined contact surface to the tissue so that the contact surface of the applanation plate forms a well-defined optical interface with the tissue. This well-defined interface can facilitate transmission and focusing of laser light into the tissue to control or reduce optical aberrations or variations (such as due to specific eye optical properties or changes that occur with surface drying) that are most critical at the air-tissue interface, which in the eye is at the anterior surface of the cornea. A number of contact lenses have been designed for various applications and targets inside the eye and other tissues, including ones that are disposable or reusable. The contact glass or applanation plate on the surface of the target tissue is used as a reference plate relative to which laser pulses are focused through the adjustment of focusing elements within the laser delivery system relative. Inherent in such an approach are the additional benefits afforded by the contact glass or applanation plate described previously, including control of the optical qualities of the tissue surface. Accordingly, laser pulses can be accurately placed at a high speed at a desired location (interaction point) in the target tissue relative to the applanation reference plate with little optical distortion of the laser pulses.

The optical imaging device 1030 in FIG. 7 captures images of the target tissue 1001 via the applanation plate. The control module 1040 processes the captured images to extract position information from the captured images and uses the extracted position information as a position reference or guide to control the position and focus of the surgical laser beam 1022. This imaging-guided laser surgery can be implemented without relying on the applanation plate as a position reference because the position of the applanation plate tends to change due to various factors as discussed above. Hence, although the applanation plate provides a desired optical interface for the surgical laser beam to enter the target tissue and to capture images of the target tissue, it may be difficult to use the applanation plate as a position reference to align and control the position and focus of the surgical laser beam for accurate delivery of laser pulses. The imaging-guided control of the position and focus of the surgical laser beam based on the imaging device 1030 and the control module 1040 allows the images of the target tissue 1001, e.g., images of inner structures of an eye, to be used as position references, without using the applanation plate to provide a position reference.

In addition to the physical effects of applanation that disproportionably affect the localization of internal tissue structures, in some surgical processes, it may be desirable for a targeting system to anticipate or account for nonlinear characteristics of photodisruption which can occur when using short pulse duration lasers. Photodisruption can cause complications in beam alignment and beam targeting. For example, one of the nonlinear optical effects in the tissue material when interacting with laser pulses during the photodisruption is that the refractive index of the tissue material experienced by the laser pulses is no longer a constant but varies with the intensity of the light. Because the intensity of the light in the laser pulses varies spatially within the pulsed laser beam, along and across the propagation direction of the pulsed laser beam, the refractive index of the tissue material also varies spatially. One consequence of this nonlinear refractive index is self-focusing or self-defocusing in the tissue material that changes the actual focus of and shifts the position of the focus of the pulsed laser beam inside the tissue. Therefore, a precise alignment of the pulsed laser beam to each target tissue position in the target tissue may also need to account for the nonlinear optical effects of the tissue material on the laser beam. The energy of the laser pulses may be adjusted to deliver the same physical effect in different regions of the target due to different physical characteristics, such as hardness, or due to optical considerations such as absorption or scattering of laser pulse light traveling to a particular region. In such cases, the differences in non-linear focusing effects between pulses of different energy values can also affect the laser alignment and laser targeting of the surgical pulses. In this regard, the direct images obtained from the target issue by the imaging device 1030 can be used to monitor the actual position of the surgical laser beam 1022 which reflects the combined effects of nonlinear optical effects in the target tissue and provide position references for control of the beam position and beam focus.

The techniques, apparatus and systems described here can be used in combination of an applanation plate to provide control of the surface shape and hydration, to reduce optical distortion, and provide for precise localization of photodisruption to internal structures through the applanated surface. The imaging-guided control of the beam position and focus described here can be applied to surgical systems and procedures that use means other than applanation plates to fix the eye, including the use of a suction ring which can lead to distortion or movement of the surgical target.

The following sections first describe examples of techniques, apparatus and systems for automated imaging-guided laser surgery based on varying degrees of integration of imaging functions into the laser control part of the systems. An optical or other modality imaging module, such as an OCT imaging module, can be used to direct a probe light or other type of beam to capture images of a target tissue, e.g., structures inside an eye. A surgical laser beam of laser pulses such as femtosecond or picosecond laser pulses can be guided by position information in the captured images to control the focusing and positioning of the surgical laser beam during the surgery. Both the surgical laser beam and the probe light beam can be sequentially or simultaneously directed to the target tissue during the surgery so that the surgical laser beam can be controlled based on the captured images to ensure precision and accuracy of the surgery.

Such imaging-guided laser surgery can be used to provide accurate and precise focusing and positioning of the surgical laser beam during the surgery because the beam control is based on images of the target tissue following applanation or fixation of the target tissue, either just before or nearly simultaneously with delivery of the surgical pulses. Notably, certain parameters of the target tissue such as the eye measured before the surgery may change during the surgery due to various factor such as preparation of the target tissue (e.g., fixating the eye to an applanation lens) and the alternation of the target tissue by the surgical operations. Therefore, measured parameters of the target tissue prior to such factors and/or the surgery may no longer reflect the physical conditions of the target tissue during the surgery. The present imaging-guided laser surgery can mitigate technical issues in connection with such changes for focusing and positioning the surgical laser beam before and during the surgery.

The present imaging-guided laser surgery may be effectively used for accurate surgical operations inside a target tissue. For example, when performing laser surgery inside the eye, laser light is focused inside the eye to achieve optical breakdown of the targeted tissue and such optical interactions can change the internal structure of the eye. For example, the crystalline lens can change its position, shape, thickness and diameter during accommodation, not only between prior measurement and surgery but also during surgery. Attaching the eye to the surgical instrument by mechanical means can change the shape of the eye in a not well defined way and further, the change can vary during surgery due to various factors, e.g., patient movement. Attaching means include fixating the eye with a suction ring and applanating the eye with a flat or curved lens. These changes amount to as much as a few millimeters. Mechanically referencing and fixating the surface of the eye such as the anterior surface of the cornea or limbus does not work well when performing precision laser microsurgery inside the eye.

The post preparation or near simultaneous imaging in the present imaging-guided laser surgery can be used to establish three-dimensional positional references between the inside features of the eye and the surgical instrument in an environment where changes occur prior to and during surgery. The positional reference information provided by the imaging prior to applanation and/or fixation of the eye, or during the actual surgery reflects the effects of changes in the eye and thus provides an accurate guidance to focusing and positioning of the surgical laser beam. A system based on the present imaging-guided laser surgery can be configured to be simple in structure and cost efficient. For example, a portion of the optical components associated with guiding the surgical laser beam can be shared with optical components for guiding the probe light beam for imaging the target tissue to simplify the device structure and the optical alignment and calibration of the imaging and surgical light beams.

The imaging-guided laser surgical systems described below use the OCT imaging as an example of an imaging instrument and other non-OCT imaging devices may also be used to capture images for controlling the surgical lasers during the surgery. As illustrated in the examples below, integration of the imaging and surgical subsystems can be implemented to various degrees. In the simplest form without integrating hardware, the imaging and laser surgical subsystems are separated and can communicate to one another through interfaces. Such designs can provide flexibility in the designs of the two subsystems. Integration between the two subsystems, by some hardware components such as a patient interface, further expands the functionality by offering better registration of surgical area to the hardware components, more accurate calibration and may improve workflow. As the degree of integration between the two subsystems increases, such a system may be made increasingly cost-efficient and compact and system calibration will be further simplified and more stable over time. Examples for imaging-guided laser systems in FIGS. 8-16 are integrated at various degrees of integration.

One implementation of a present imaging-guided laser surgical system, for example, includes a surgical laser that produces a surgical laser beam of surgical laser pulses that cause surgical changes in a target tissue under surgery; a patient interface mount that engages a patient interface in contact with the target tissue to hold the target tissue in position; and a laser beam delivery module located between the surgical laser and the patient interface and configured to direct the surgical laser beam to the target tissue through the patient interface. This laser beam delivery module is operable to scan the surgical laser beam in the target tissue along a predetermined surgical pattern. This system also includes a laser control module that controls operation of the surgical laser and controls the laser beam delivery module to produce the predetermined surgical pattern and an OCT module positioned relative to the patient interface to have a known spatial relation with respect to the patient interface and the target issue fixed to the patient interface. The OCT module is configured to direct an optical probe beam to the target tissue and receive returned probe light of the optical probe beam from the target tissue to capture OCT images of the target tissue while the surgical laser beam is being directed to the target tissue to perform an surgical operation so that the optical probe beam and the surgical laser beam are simultaneously present in the target tissue. The OCT module is in communication with the laser control module to send information of the captured OCT images to the laser control module.

In addition, the laser control module in this particular system responds to the information of the captured OCT images to operate the laser beam delivery module in focusing and scanning of the surgical laser beam and adjusts the focusing and scanning of the surgical laser beam in the target tissue based on positioning information in the captured OCT images.

In some implementations, acquiring a complete image of a target tissue may not be necessary for registering the target to the surgical instrument and it may be sufficient to acquire a portion of the target tissue, e.g., a few points from the surgical region such as natural or artificial landmarks. For example, a rigid body has six degrees of freedom in 3D space and six independent points would be sufficient to define the rigid body. When the exact size of the surgical region is not known, additional points are needed to provide the positional reference. In this regard, several points can be used to determine the position and the curvature of the anterior and posterior surfaces, which are normally different, and the thickness and diameter of the crystalline lens of the human eye. Based on these data a body made up from two halves of ellipsoid bodies with given parameters can approximate and visualize a crystalline lens for practical purposes. In another implementation, information from the captured image may be combined with information from other sources, such as pre-operative measurements of lens thickness that are used as an input for the controller.

Figure 8:
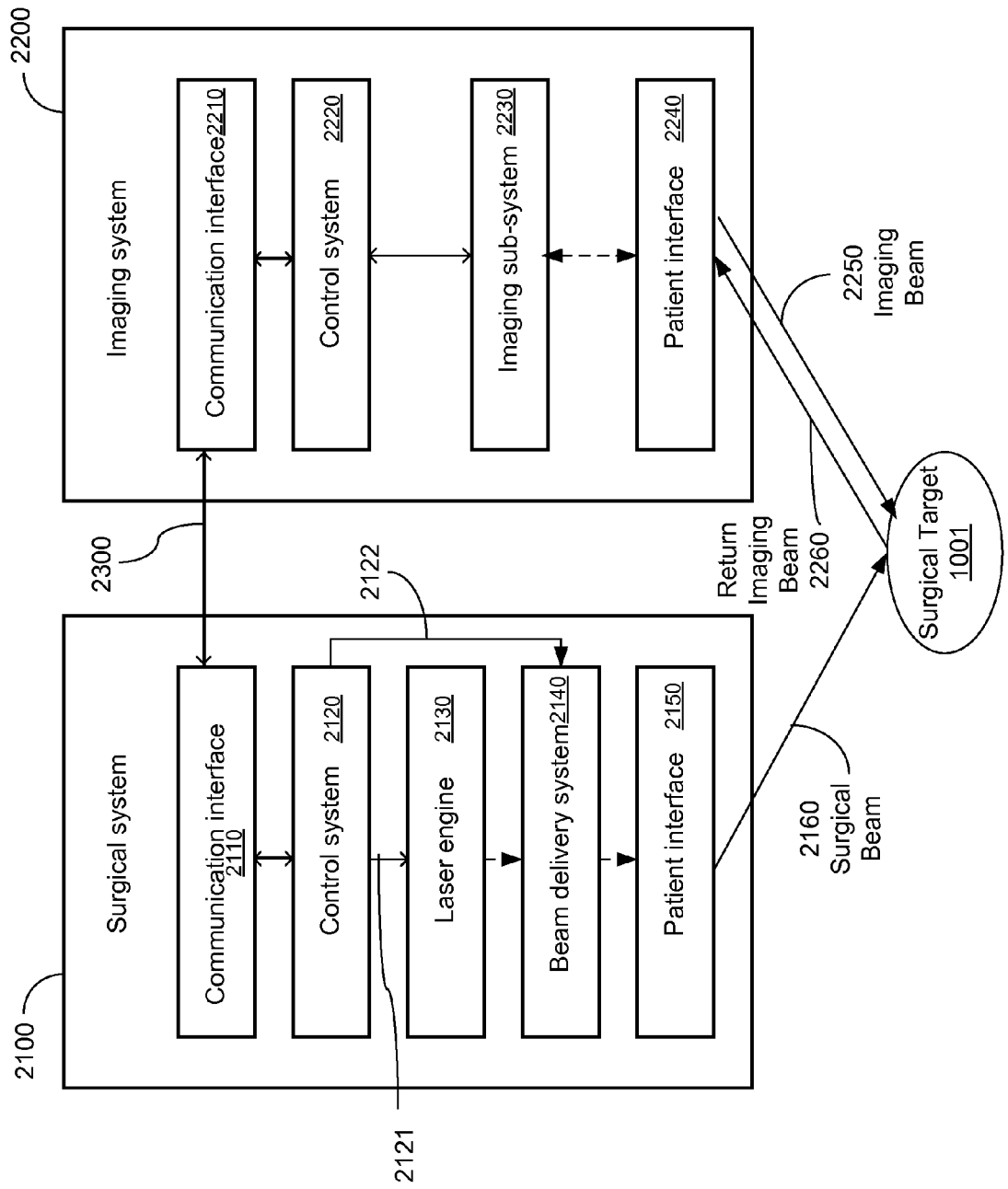
FIGS. 8-16 show examples of imaging-guided laser surgical systems with varying degrees of integration of a laser surgical system and an imaging system.

FIG. 8 shows one example of an imaging-guided laser surgical system with separated laser surgical system 2100 and imaging system 2200. The laser surgical system 2100 includes a laser engine 2130 with a surgical laser that produces a surgical laser beam 2160 of surgical laser pulses. A laser beam delivery module 2140 is provided to direct the surgical laser beam 2160 from the laser engine 2130 to the target tissue 1001 through a patient interface 2150 and is operable to scan the surgical laser beam 2160 in the target tissue 1001 along a predetermined surgical pattern. A laser control module 2120 is provided to control the operation of the surgical laser in the laser engine 2130 via a communication channel 2121 and controls the laser beam delivery module 2140 via a communication channel 2122 to produce the predetermined surgical pattern. A patient interface mount is provided to engage the patient interface 2150 in contact with the target tissue 1001 to hold the target tissue 1001 in position. The patient interface 2150 can be implemented to include a contact lens or applanation lens with a flat or curved surface to conformingly engage to the anterior surface of the eye and to hold the eye in position.

The imaging system 2200 in FIG. 8 can be an OCT module positioned relative to the patient interface 2150 of the surgical system 2100 to have a known spatial relation with respect to the patient interface 2150 and the target issue 1001 fixed to the patient interface 2150. This OCT module 2200 can be configured to have its own patient interface 2240 for interacting with the target tissue 1001. The imaging system 2200 includes an imaging control module 2220 and an imaging sub-system 2230. The sub-system 2230 includes a light source for generating imaging beam 2250 for imaging the target 1001 and an imaging beam delivery module to direct the optical probe beam or imaging beam 2250 to the target tissue 1001 and receive returned probe light 2260 of the optical imaging beam 2250 from the target tissue 1001 to capture OCT images of the target tissue 1001. Both the optical imaging beam 2250 and the surgical beam 2160 can be simultaneously directed to the target tissue 1001 to allow for sequential or simultaneous imaging and surgical operation.

As illustrated in FIG. 8, communication interfaces 2110 and 2210 are provided in both the laser surgical system 2100 and the imaging system 2200 to facilitate the communications between the laser control by the laser control module 2120 and imaging by the imaging system 2200 so that the OCT module 2200 can send information of the captured OCT images to the laser control module 2120. The laser control module 2120 in this system responds to the information of the captured OCT images to operate the laser beam delivery module 2140 in focusing and scanning of the surgical laser beam 2160 and dynamically adjusts the focusing and scanning of the surgical laser beam 2160 in the target tissue 1001 based on positioning information in the captured OCT images. The integration between the laser surgical system 2100 and the imaging system 2200 is mainly through communication between the communication interfaces 2110 and 2210 at the software level.

In this and other examples, various subsystems or devices may also be integrated. For example, certain diagnostic instruments such as wavefront aberrometers, corneal topography measuring devices may be provided in the system, or pre-operative information from these devices can be utilized to augment intra-operative imaging.

Figure 9:
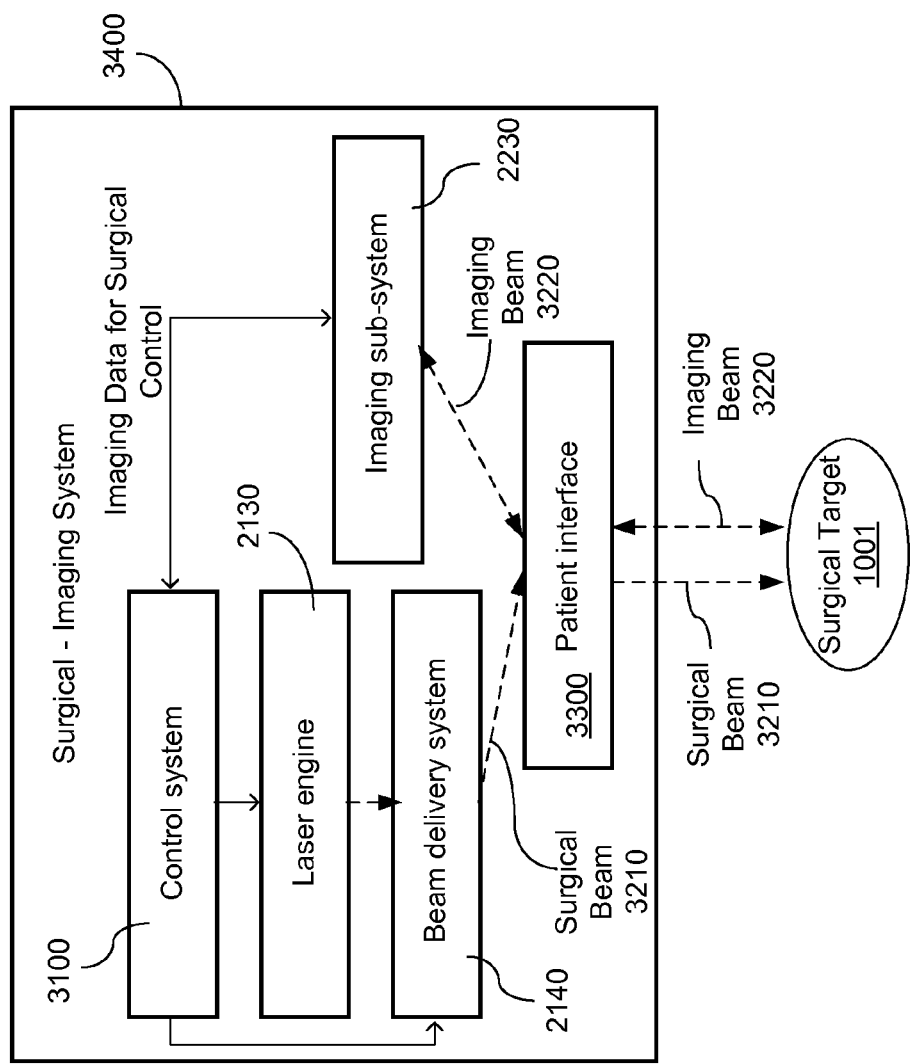

FIG. 9 shows an example of an imaging-guided laser surgical system with additional integration features. The imaging and surgical systems share a common patient interface 3300 which immobilizes target tissue 1001 (e.g., the eye) without having two separate patient interfaces as in FIG. 8. The surgical beam 3210 and the imaging beam 3220 are combined at the patient interface 3330 and are directed to the target 1001 by the common patient interface 3300. In addition, a common control module 3100 is provided to control both the imaging sub-system 2230 and the surgical part (the laser engine 2130 and the beam delivery system 2140). This increased integration between imaging and surgical parts allows accurate calibration of the two subsystems and the stability of the position of the patient and surgical volume. A common housing 3400 is provided to enclose both the surgical and imaging subsystems. When the two systems are not integrated into a common housing, the common patient interface 3300 can be part of either the imaging or the surgical subsystem.

Figure 10:
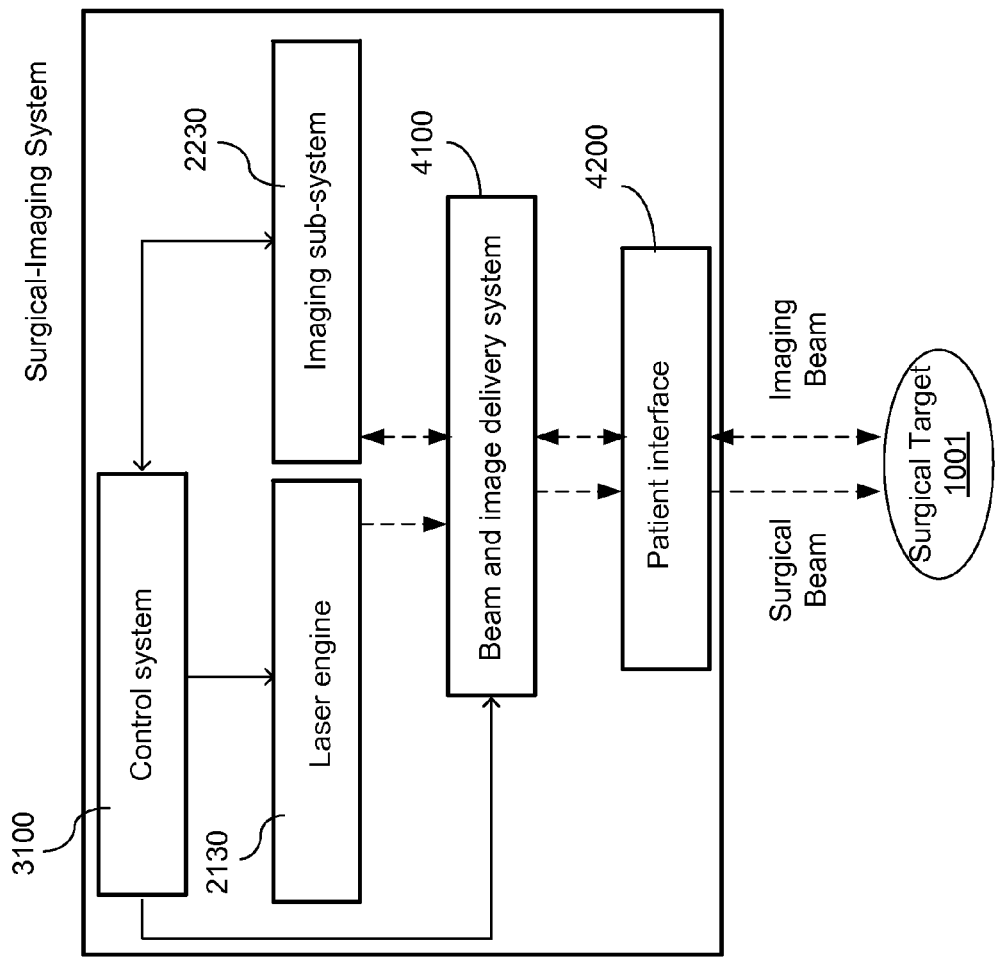

FIG. 10 shows an example of an imaging-guided laser surgical system where the laser surgical system and the imaging system share both a common beam delivery module 4100 and a common patient interface 4200. This integration further simplifies the system structure and system control operation.

In one implementation, the imaging system in the above and other examples can be an optical computed tomography (OCT) system and the laser surgical system is a femtosecond or picosecond laser based ophthalmic surgical system. In OCT, light from a low coherence, broadband light source such as a super luminescent diode is split into separate reference and signal beams. The signal beam is the imaging beam sent to the surgical target and the returned light of the imaging beam is collected and recombined coherently with the reference beam to form an interferometer. Scanning the signal beam perpendicularly to the optical axis of the optical train or the propagation direction of the light provides spatial resolution in the x-y direction while depth resolution comes from extracting differences between the path lengths of the reference arm and the returned signal beam in the signal arm of the interferometer. While the x-y scanner of different OCT implementations are essentially the same, comparing the path lengths and getting Z-scan information can happen in different ways. In one implementation known as the time domain OCT, for example, the reference arm is continuously varied to change its path length while a photodetector detects interference modulation in the intensity of the re-combined beam. In a different implementation, the reference arm is essentially static and the spectrum of the combined light is analyzed for interference. The Fourier transform of the spectrum of the combined beam provides spatial information on the scattering from the interior of the sample. This method is known as the spectral domain or Fourier OCT method. In a different implementation known as a frequency swept OCT (S. R. Chinn, et. al., Opt. Lett. 22, 1997), a narrowband light source is used with its frequency swept rapidly across a spectral range. Interference between the reference and signal arms is detected by a fast detector and dynamic signal analyzer. An external cavity tuned diode laser or frequency tuned of frequency domain mode-locked (FDML) laser developed for this purpose (R. Huber et. Al. Opt. Express, 13, 2005) (S. H. Yun, IEEE J. of Sel. Q. El. 3(4) p. 1087-1096, 1997) can be used in these examples as a light source. A femtosecond laser used as a light source in an OCT system can have sufficient bandwidth and can provide additional benefits of increased signal to noise ratios.

The OCT imaging device in the systems in this document can be used to perform various imaging functions. For example, the OCT can be used to suppress complex conjugates resulting from the optical configuration of the system or the presence of the applanation plate, capture OCT images of selected locations inside the target tissue to provide three-dimensional positioning information for controlling focusing and scanning of the surgical laser beam inside the target tissue, or capture OCT images of selected locations on the surface of the target tissue or on the applanation plate to provide positioning registration for controlling changes in orientation that occur with positional changes of the target, such as from upright to supine. The OCT can be calibrated by a positioning registration process based on placement of marks or markers in one positional orientation of the target that can then be detected by the OCT module when the target is in another positional orientation. In other implementations, the OCT imaging system can be used to produce a probe light beam that is polarized to optically gather the information on the internal structure of the eye. The laser beam and the probe light beam may be polarized in different polarizations. The OCT can include a polarization control mechanism that controls the probe light used for said optical tomography to polarize in one polarization when traveling toward the eye and in a different polarization when traveling away from the eye. The polarization control mechanism can include, e.g., a wave-plate or a Faraday rotator.

The system in FIG. 10 is shown as a spectral OCT configuration and can be configured to share the focusing optics part of the beam delivery module between the surgical and the imaging systems. The main requirements for the optics are related to the operating wavelength, image quality, resolution, distortion etc. The laser surgical system can be a femtosecond laser system with a high numerical aperture system designed to achieve diffraction limited focal spot sizes, e.g., about 2 to 3 micrometers. Various femtosecond ophthalmic surgical lasers can operate at various wavelengths such as wavelengths of around 1.05 micrometer. The operating wavelength of the imaging device can be selected to be close to the laser wavelength so that the optics is chromatically compensated for both wavelengths. Such a system may include a third optical channel, a visual observation channel such as a surgical microscope, to provide an additional imaging device to capture images of the target tissue. If the optical path for this third optical channel shares optics with the surgical laser beam and the light of the OCT imaging device, the shared optics can be configured with chromatic compensation in the visible spectral band for the third optical channel and the spectral bands for the surgical laser beam and the OCT imaging beam.

Figure 11:
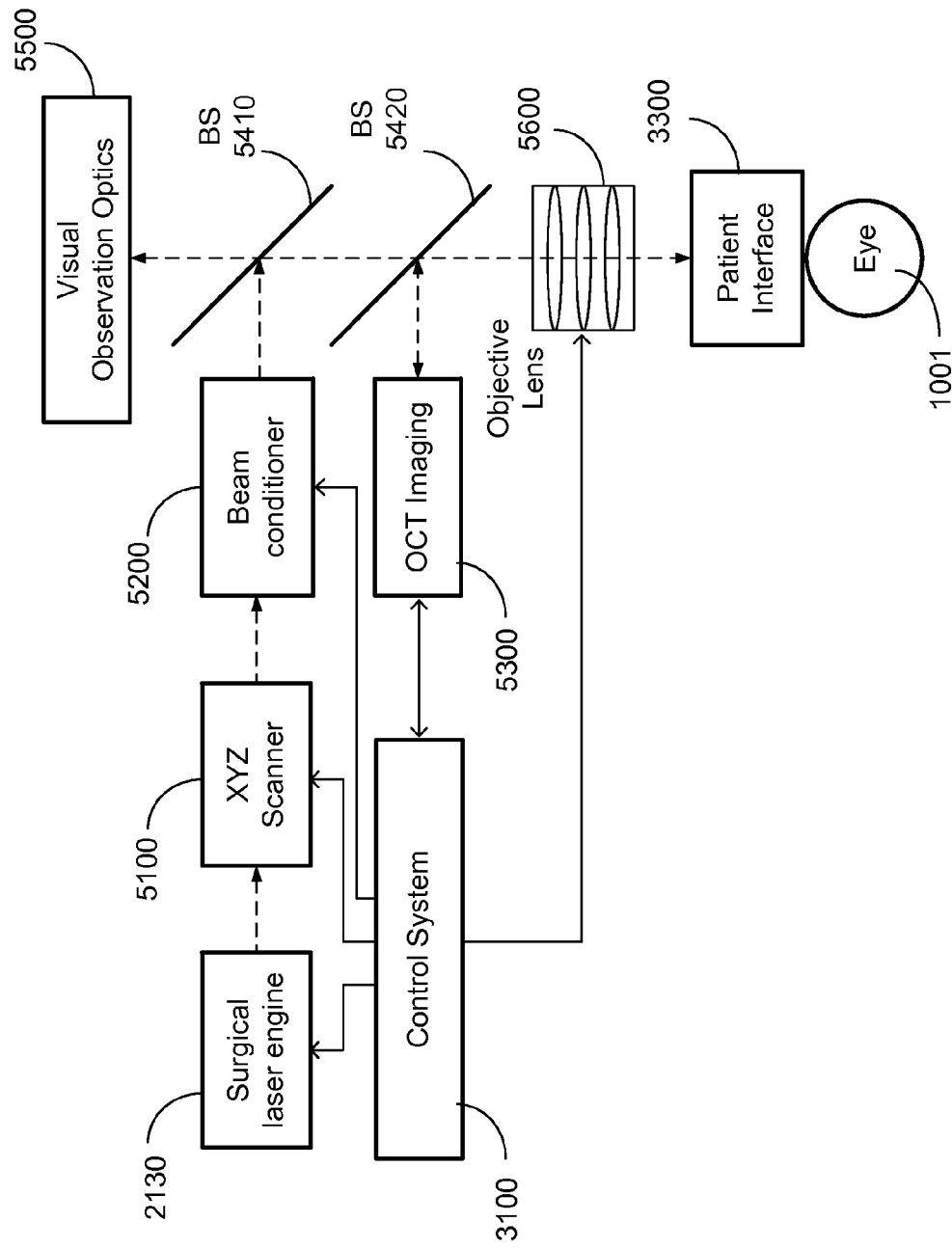

FIG. 11 shows a particular example of the design in FIG. 9 where the scanner 5100 for scanning the surgical laser beam and the beam conditioner 5200 for conditioning (collimating and focusing) the surgical laser beam are separate from the optics in the OCT imaging module 5300 for controlling the imaging beam for the OCT. The surgical and imaging systems share an objective lens 5600 module and the patient interface 3300. The objective lens 5600 directs and focuses both the surgical laser beam and the imaging beam to the patient interface 3300 and its focusing is controlled by the control module 3100. Two beam splitters 5410 and 5420 are provided to direct the surgical and imaging beams. The beam splitter 5420 is also used to direct the returned imaging beam back into the OCT imaging module 5300. Two beam splitters 5410 and 5420 also direct light from the target 1001 to a visual observation optics unit 5500 to provide direct view or image of the target 1001. The unit 5500 can be a lens imaging system for the surgeon to view the target 1001 or a camera to capture the image or video of the target 1001. Various beam splitters can be used, such as dichroic and polarization beam splitters, optical grating, holographic beam splitter or a combinations of these.

In some implementations, the optical components may be appropriately coated with antireflection coating for both the surgical and for the OCT wavelength to reduce glare from multiple surfaces of the optical beam path. Reflections would otherwise reduce the throughput of the system and reduce the signal to noise ratio by increasing background light in the OCT imaging unit. One way to reduce glare in the OCT is to rotate the polarization of the return light from the sample by wave-plate of Faraday isolator placed close to the target tissue and orient a polarizer in front of the OCT detector to preferentially detect light returned from the sample and suppress light scattered from the optical components.

In a laser surgical system, each of the surgical laser and the OCT system can have a beam scanner to cover the same surgical region in the target tissue. Hence, the beam scanning for the surgical laser beam and the beam scanning for the imaging beam can be integrated to share common scanning devices.

Figure 12:
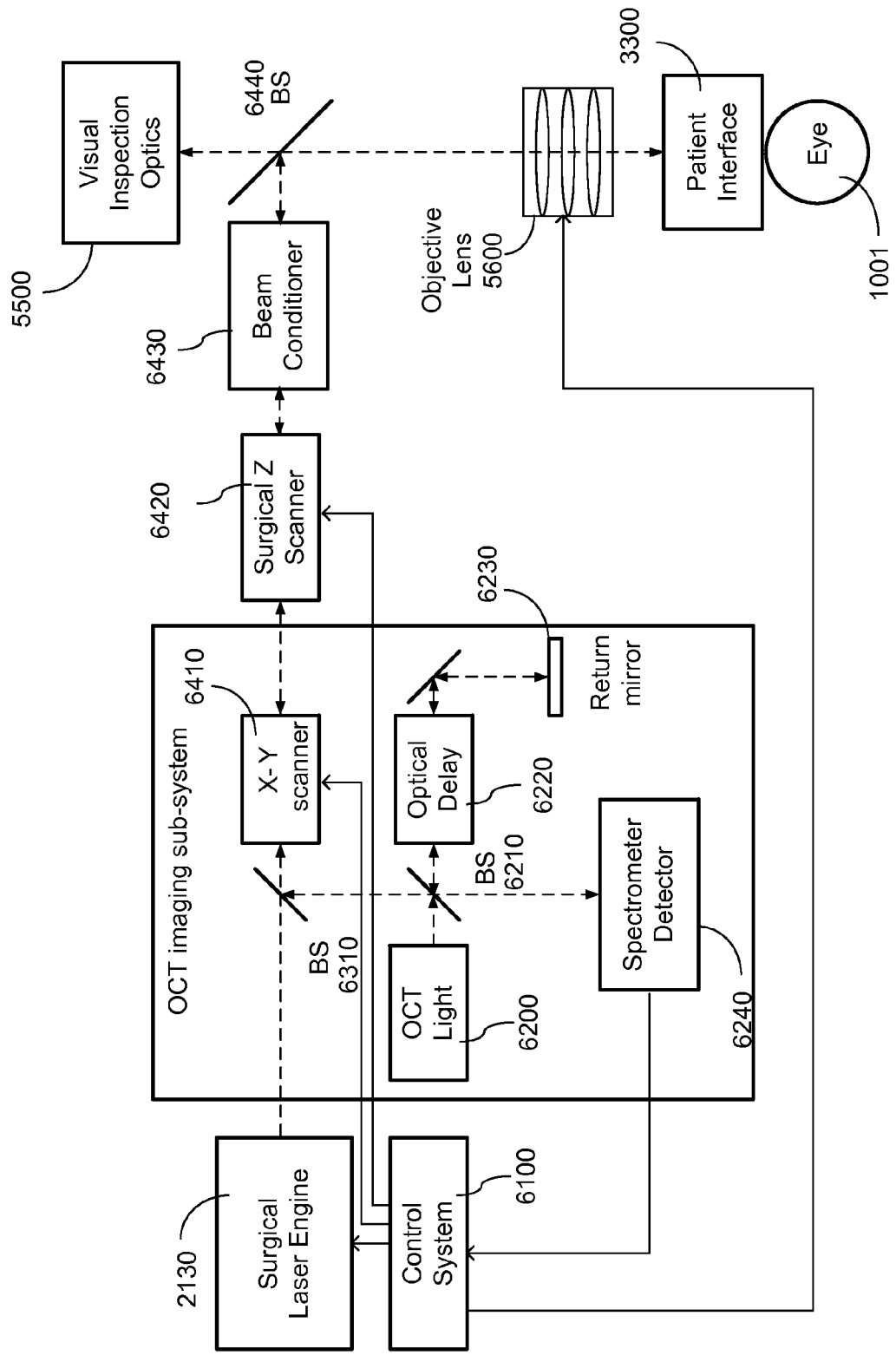

FIG. 12 shows an example of such a system in detail. In this implementation the x-y scanner 6410 and the z scanner 6420 are shared by both subsystems. A common control 6100 is provided to control the system operations for both surgical and imaging operations. The OCT sub-system includes an OCT light source 6200 that produce the imaging light that is split into an imaging beam and a reference beam by a beam splitter 6210. The imaging beam is combined with the surgical beam at the beam splitter 6310 to propagate along a common optical path leading to the target 1001. The scanners 6410 and 6420 and the beam conditioner unit 6430 are located downstream from the beam splitter 6310. A beam splitter 6440 is used to direct the imaging and surgical beams to the objective lens 5600 and the patient interface 3300.

In the OCT sub-system, the reference beam transmits through the beam splitter 6210 to an optical delay device 6220 and is reflected by a return mirror 6230. The returned imaging beam from the target 1001 is directed back to the beam splitter 6310 which reflects at least a portion of the returned imaging beam to the beam splitter 6210 where the reflected reference beam and the returned imaging beam overlap and interfere with each other. A spectrometer detector 6240 is used to detect the interference and to produce OCT images of the target 1001. The OCT image information is sent to the control system 6100 for controlling the surgical laser engine 2130, the scanners 6410 and 6420 and the objective lens 5600 to control the surgical laser beam. In one implementation, the optical delay device 6220 can be varied to change the optical delay to detect various depths in the target tissue 1001.

If the OCT system is a time domain system, the two subsystems use two different Z-scanners because the two scanners operate in different ways. In this example, the z scanner of the surgical system operates by changing the divergence of the surgical beam in the beam conditioner unit without changing the path lengths of the beam in the surgical beam path. On the other hand, the time domain OCT scans the z-direction by physically changing the beam path by a variable delay or by moving the position of the reference beam return mirror. After calibration, the two z-scanners can be synchronized by the laser control module. The relationship between the two movements can be simplified to a linear or polynomial dependence, which the control module can handle or alternatively calibration points can define a look-up table to provide proper scaling. Spectral/Fourier domain and frequency swept source OCT devices have no z-scanner, the length of the reference arm is static. Besides reducing costs, cross calibration of the two systems will be relatively straightforward. There is no need to compensate for differences arising from image distortions in the focusing optics or from the differences of the scanners of the two systems since they are shared.

In practical implementations of the surgical systems, the focusing objective lens 5600 is slidably or movably mounted on a base and the weight of the objective lens is balanced to limit the force on the patient's eye. The patient interface 3300 can include an applanation lens attached to a patient interface mount. The patient interface mount is attached to a mounting unit, which holds the focusing objective lens. This mounting unit is designed to ensure a stable connection between the patient interface and the system in case of unavoidable movement of the patient and allows gentler docking of the patient interface onto the eye. Various implementations for the focusing objective lens can be used and one example is described in U.S. Pat. No. 5,336,215 to Hsueh. This presence of an adjustable focusing objective lens can change the optical path length of the optical probe light as part of the optical interferometer for the OCT sub-system. Movement of the objective lens 5600 and patient interface 3300 can change the path length differences between the reference beam and the imaging signal beam of the OCT in an uncontrolled way and this may degrade the OCT depth information detected by the OCT. This would happen not only in time-domain but also in spectral/Fourier domain and frequency-swept OCT systems.

Figure 13:
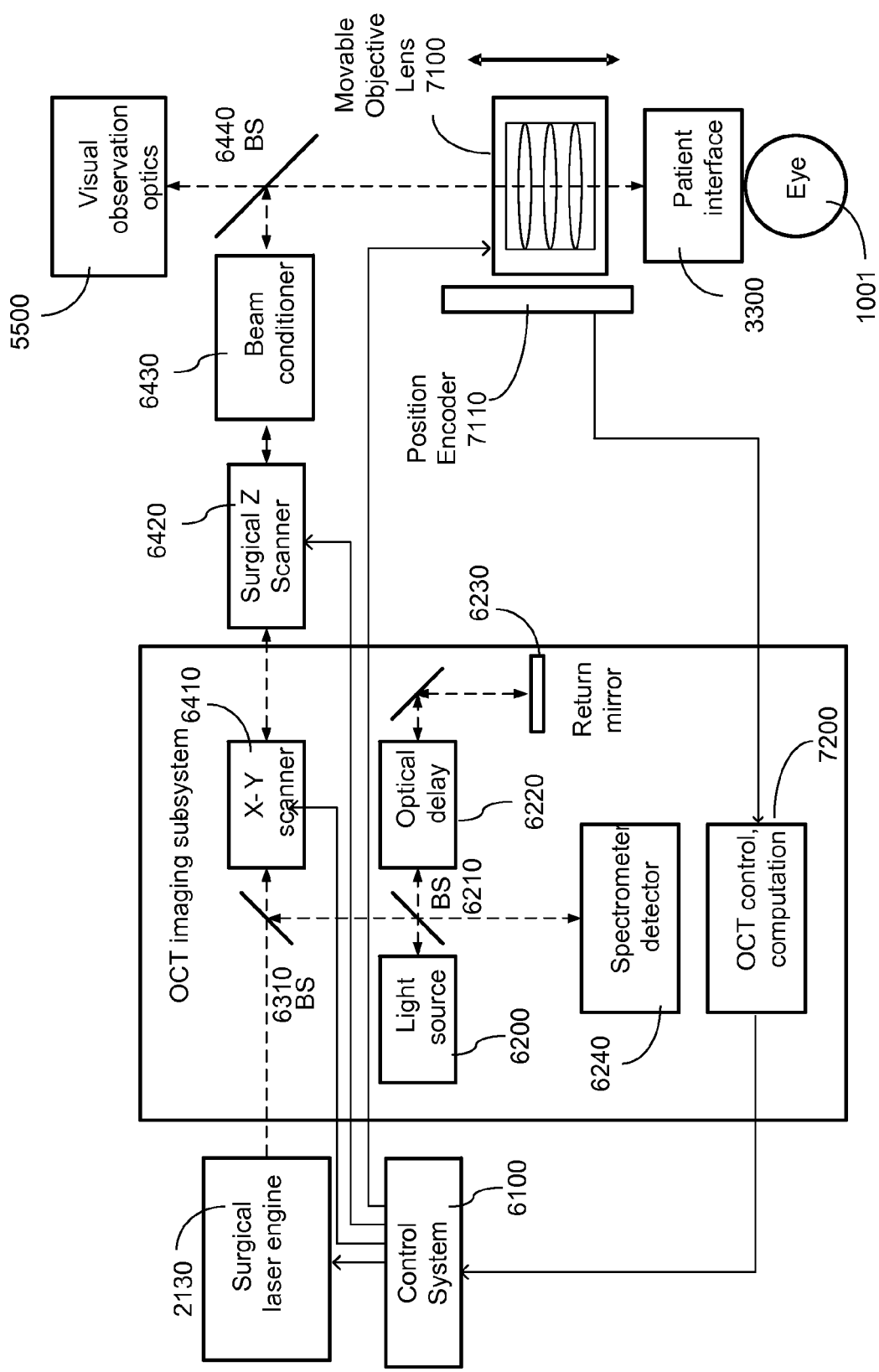
Figure 14:
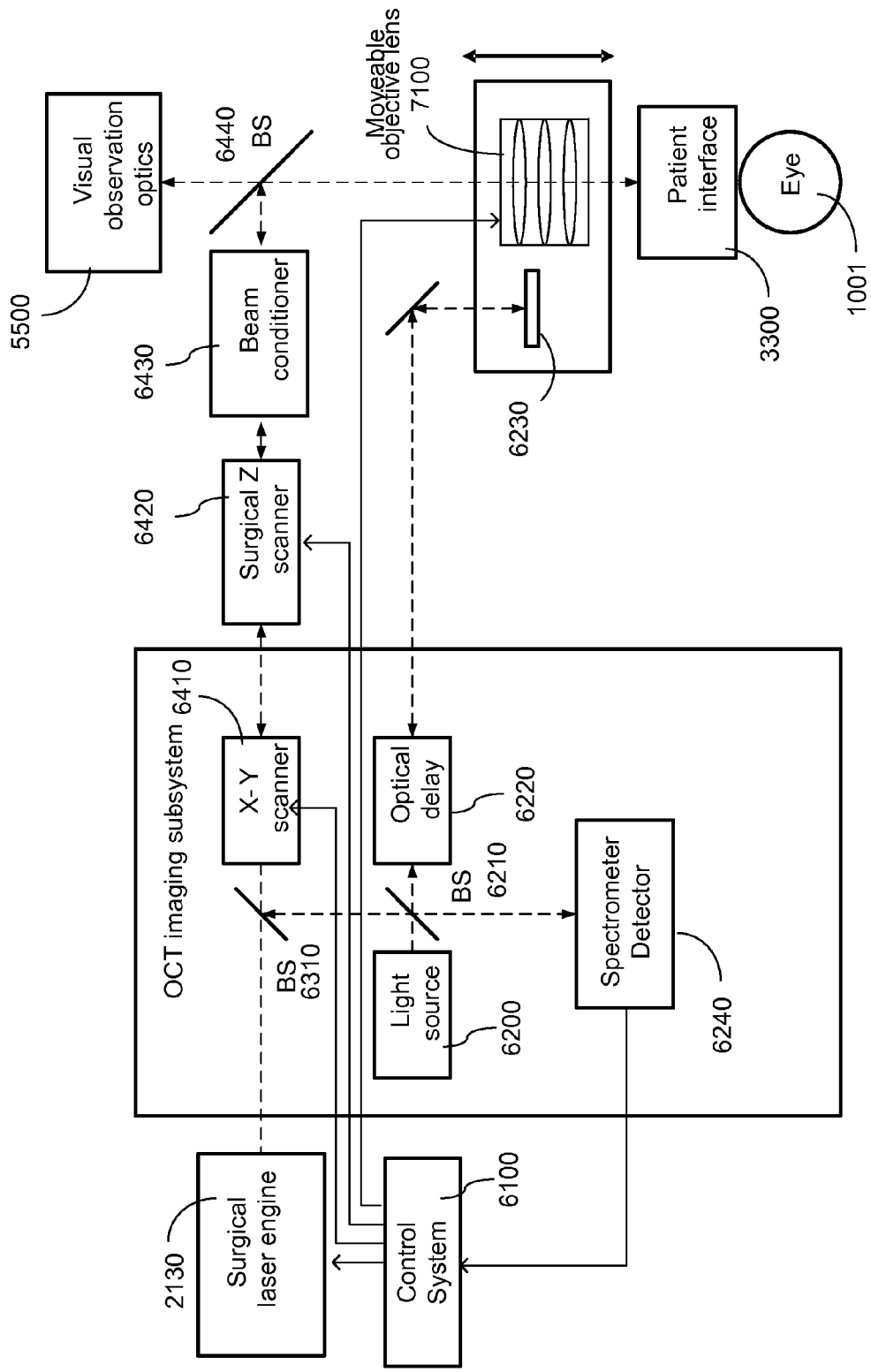

FIGS. 13-14 show exemplary imaging-guided laser surgical systems that address the technical issue associated with the adjustable focusing objective lens.

The system in FIG. 13 provides a position sensing device 7110 coupled to the movable focusing objective lens 7100 to measure the position of the objective lens 7100 on a slideable mount and communicates the measured position to a control module 7200 in the OCT system. The control system 6100 can control and move the position of the objective lens 7100 to adjust the optical path length traveled by the imaging signal beam for the OCT operation and the position of the lens 7100 is measured and monitored by the position encoder 7110 and direct fed to the OCT control 7200. The control module 7200 in the OCT system applies an algorithm, when assembling a 3D image in processing the OCT data, to compensate for differences between the reference arm and the signal arm of the interferometer inside the OCT caused by the movement of the focusing objective lens 7100 relative to the patient interface 3300. The proper amount of the change in the position of the lens 7100 computed by the OCT control module 7200 is sent to the control 6100 which controls the lens 7100 to change its position.

FIG. 14 shows another exemplary system where the return mirror 6230 in the reference arm of the interferometer of the OCT system or at least one part in an optical path length delay assembly of the OCT system is rigidly attached to the movable focusing objective lens 7100 so the signal arm and the reference arm undergo the same amount of change in the optical path length when the objective lens 7100 moves. As such, the movement of the objective lens 7100 on the slide is automatically compensated for path-length differences in the OCT system without additional need for a computational compensation.

The above examples for imaging-guided laser surgical systems, the laser surgical system and the OCT system use different light sources. In an even more complete integration between the laser surgical system and the OCT system, a femtosecond surgical laser as a light source for the surgical laser beam can also be used as the light source for the OCT system.

Figure 15:
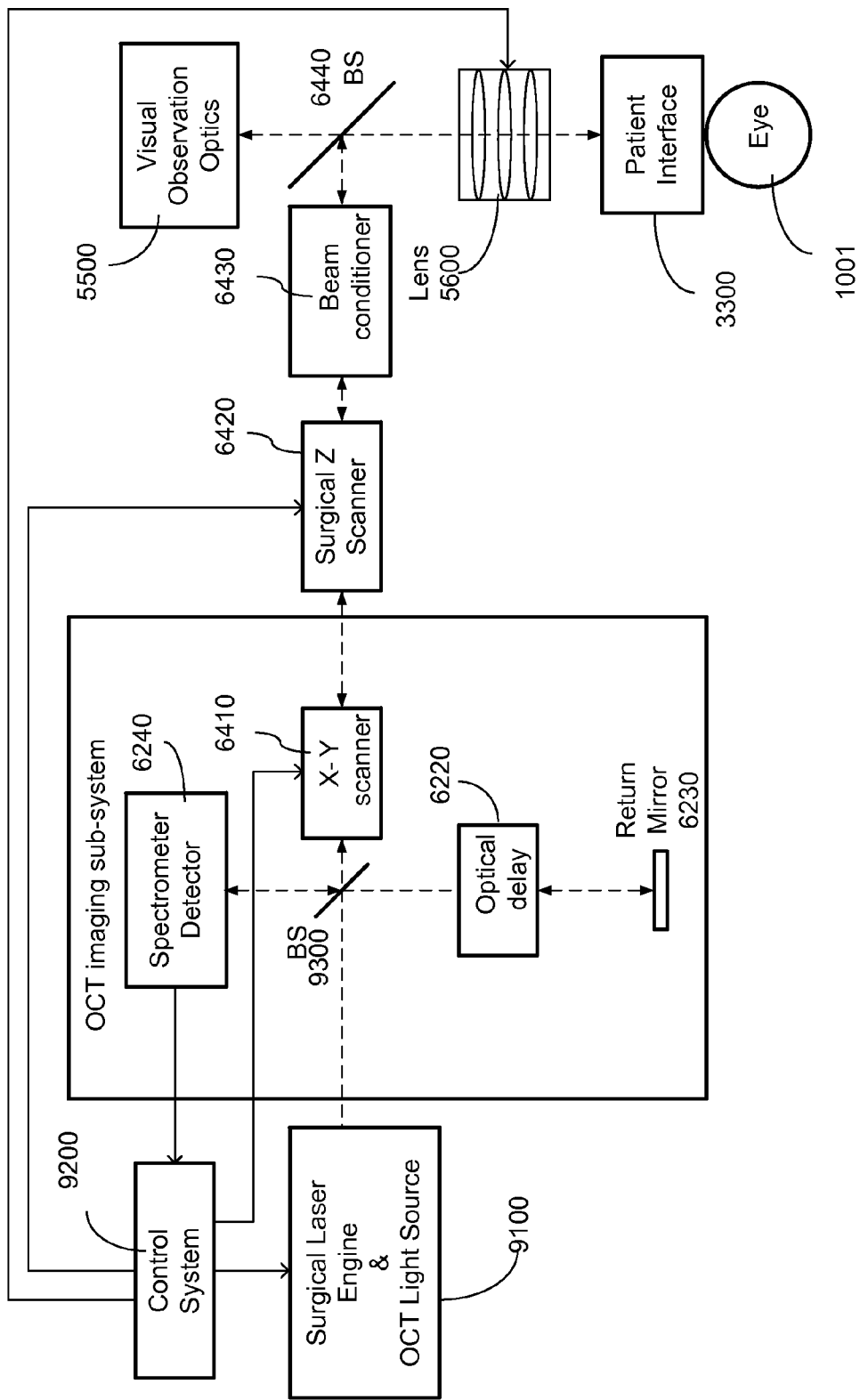

FIG. 15 shows an example where a femtosecond pulse laser in a light module 9100 is used to generate both the surgical laser beam for surgical operations and the probe light beam for OCT imaging. A beam splitter 9300 is provided to split the laser beam into a first beam as both the surgical laser beam and the signal beam for the OCT and a second beam as the reference beam for the OCT. The first beam is directed through an x-y scanner 6410 which scans the beam in the x and y directions perpendicular to the propagation direction of the first beam and a second scanner (z scanner) 6420 that changes the divergence of the beam to adjust the focusing of the first beam at the target tissue 1001. This first beam performs the surgical operations at the target tissue 1001 and a portion of this first beam is back scattered to the patient interface and is collected by the objective lens as the signal beam for the signal arm of the optical interferometer of the OCT system. This returned light is combined with the second beam that is reflected by a return mirror 6230 in the reference arm and is delayed by an adjustable optical delay element 6220 for a time-domain OCT to control the path difference between the signal and reference beams in imaging different depths of the target tissue 1001. The control system 9200 controls the system operations.

Surgical practice on the cornea has shown that a pulse duration of several hundred femtoseconds may be sufficient to achieve good surgical performance, while for OCT of a sufficient depth resolution broader spectral bandwidth generated by shorter pulses, e.g., below several tens of femtoseconds, are needed. In this context, the design of the OCT device dictates the duration of the pulses from the femtosecond surgical laser.

Figure 16:
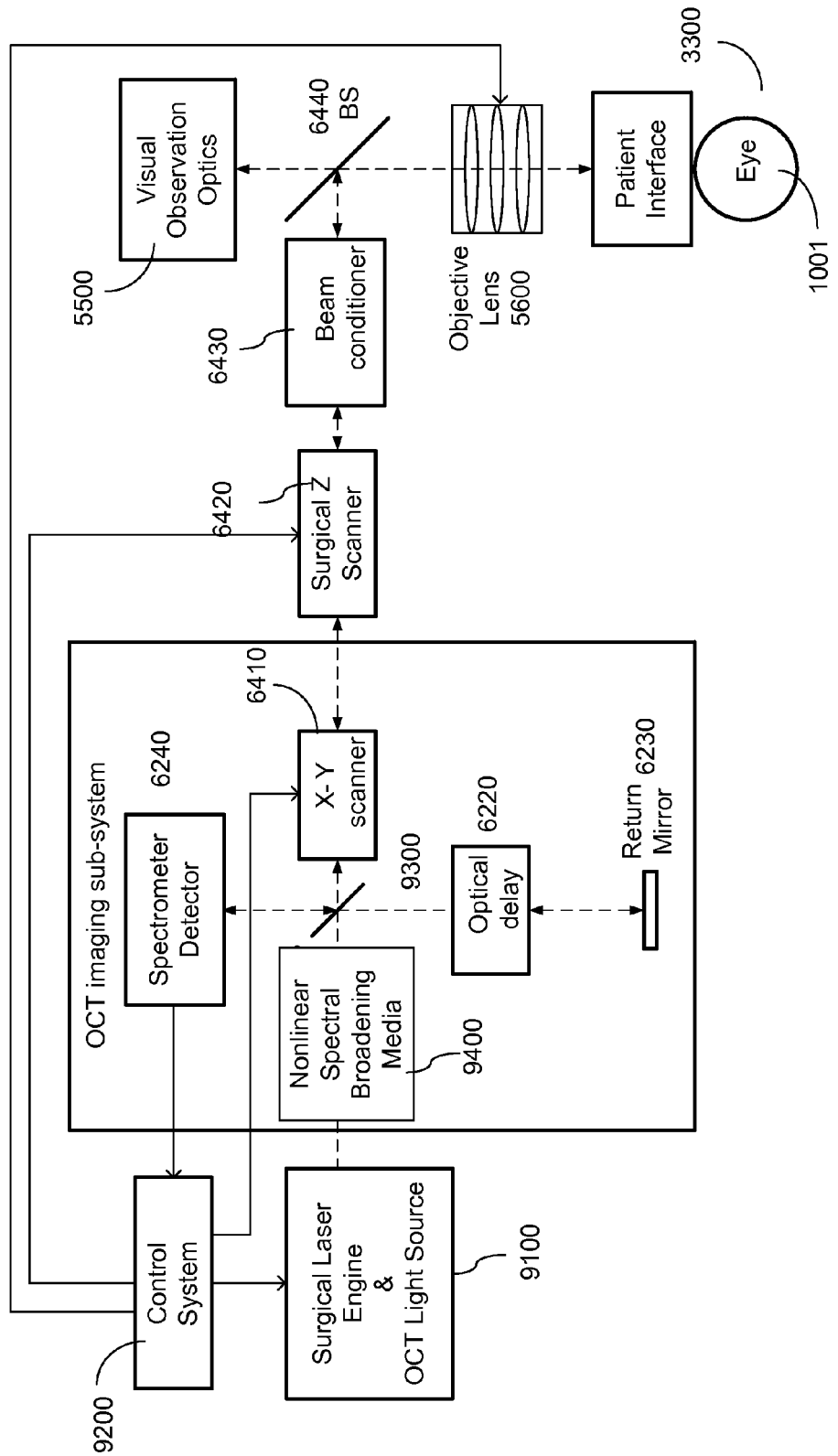

FIG. 16 shows another imaging-guided system that uses a single pulsed laser 9100 to produce the surgical light and the imaging light. A nonlinear spectral broadening media 9400 is placed in the output optical path of the femtosecond pulsed laser to use an optical non-linear process such as white light generation or spectral broadening to broaden the spectral bandwidth of the pulses from a laser source of relatively longer pulses, several hundred femtoseconds normally used in surgery. The media 9400 can be a fiber-optic material, for example. The light intensity requirements of the two systems are different and a mechanism to adjust beam intensities can be implemented to meet such requirements in the two systems. For example, beam steering mirrors, beam shutters or attenuators can be provided in the optical paths of the two systems to properly control the presence and intensity of the beam when taking an OCT image or performing surgery in order to protect the patient and sensitive instruments from excessive light intensity.

In operation, the above examples in FIGS. 8-16 can be used to perform imaging-guided laser surgery.

Figure 17:
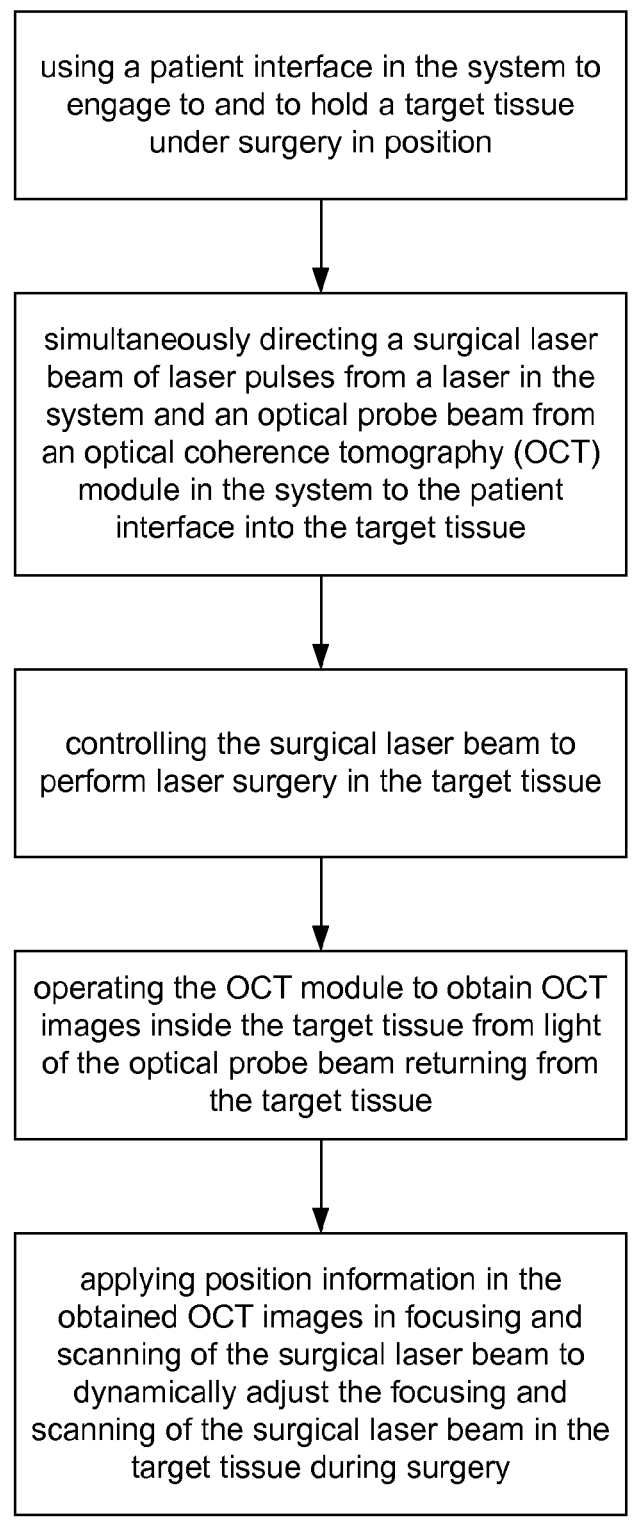
FIG. 17 shows an example of a method for performing laser surgery by suing an imaging-guided laser surgical system.

FIG. 17 shows one example of a method for performing laser surgery by using an imaging-guided laser surgical system. This method uses a patient interface in the system to engage to and to hold a target tissue under surgery in position and simultaneously directs a surgical laser beam of laser pulses from a laser in the system and an optical probe beam from the OCT module in the system to the patient interface into the target tissue. The surgical laser beam is controlled to perform laser surgery in the target tissue and the OCT module is operated to obtain OCT images inside the target tissue from light of the optical probe beam returning from the target tissue. The position information in the obtained OCT images is applied in focusing and scanning of the surgical laser beam to adjust the focusing and scanning of the surgical laser beam in the target tissue before or during surgery.

While this document contains many specifics, these should not be construed as limitations on the scope of any invention or of what may be claimed, but rather as descriptions of features specific to particular embodiments. Certain features that are described in this document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

A number of implementations of techniques and systems for imaging the eye and their applications have been disclosed. Variations and enhancements of the described implementations and other implementations can be made based on what has been described.

The invention claimed is:

1. A method for imaging an eye, comprising the steps of:
   positioning the eye relative to a Spectral Domain Optical Coherence Tomographic (SD-OCT) imaging system, the eye having a first and a second structure; and
   imaging the eye with the SD-OCT imaging system by
      selecting one of a direct image or a mirror image of the first eye-structure and generating a first image-portion, corresponding to the selected image of the first eye-structure;
      selecting one of a direct image or a mirror image of the second eye-structure and generating a second image-portion, corresponding to the selected image of the second eye-structure; and
      suppressing the non-selected images of the first and second structures.

2. The method of claim 1, wherein the generating the first and second image-portions comprises:
   performing a transformation on one of the first or second image-portions to generate a biologically representative image of the first and second structures, when
      at least one of the first or the second image-portions is a mirror image.

3. The method of claim 1, the imaging the eye step comprising:
   adjusting a reference depth of the SD-OCT imaging system
      to generate the direct and mirror images of the first and second eye-structures at corresponding image depths
      so that the direct and mirror images of the first and second eye-structures can be distinguished from each other.

4. The method of claim 3, the distinguishing the direct and mirror images of the first and second eye-structures step comprising at least one of:
   recognizing a spatial separation of the images;
   applying a pattern recognition approach;
   distinguishing a signal characteristic of the images;
   utilizing pre-existing knowledge about the eye; or
   utilizing knowledge about the eye based on a diagnostics, or
   a combination of the recited steps.

5. The method of claim 3, wherein
   the steps of adjusting the reference depth and distinguishing the direct and mirror images of the first and second eye-structures are performed iteratively.

6. The method of claim 3, wherein:
   the first structure is an anterior capsule layer of a lens of the eye; and
   the second structure is a posterior capsule layer of the lens of the eye.

7. The method of claim 6, the imaging the eye step comprising:
   adjusting the reference depth of the SD-OCT imaging system so that a depth-sequence of the first image-portion, the second image-portion and a cornea image is one of:
      direct image of the cornea—direct image of the anterior capsule layer—mirror image of the posterior capsule layer;
      direct image of the cornea—mirror image of the posterior capsule layer—direct image of the anterior capsule layer; or
      mirror image of the posterior capsule layer—direct image of the cornea—direct image of the anterior capsule layer.

8. The method of claim 3, the adjusting the reference depth step comprising one of:
   adjusting a position of a reference mirror of the SD-OCT imaging system; or
   tuning a delay element of the SD-OCT imaging system, or
   a combination of the recited steps.

9. The method of claim 3, the imaging the eye step comprising:
   a homodyne imaging.

10. The method of claim 3, wherein the imaging the eye step comprises:
    adjusting an imaging range around the reference depth
       to result in the first and the second structures being located within the imaging range.

11. The method of claim 10, wherein the adjusting the imaging range step comprises:
    adjusting at least one of a central wavelength or a wavelength resolution of the SD-OCT imaging system.

12. The method of claim 10, wherein the adjusting step comprises;
    adjusting the imaging range to be within the 0-15 mm range.

13. The method of claim 10, wherein the adjusting step comprises;
    adjusting the imaging range to be in the 5-15 mm range.

14. The method of claim 10, wherein the imaging the eye step comprises:
    adjusting a Rayleigh range around a focal depth
       to result in the imaging range being less than 4 times the Rayleigh range.

15. The method of claim 3, the adjusting the reference depth step comprising:
    adjusting the reference depth to be within the range of 2-15 mm.

16. The method of claim 1, the positioning the eye step comprising at least one of;
    docking the eye to an interface of the SD-OCT imaging system;
    immobilizing the eye; or
    minimizing a motion range of the eye relative to the SD-OCT imaging system, or
    a combination of the recited steps.

17. The method of claim 1, wherein:
    the SD-OCT imaging system is one of a
    Spectrometer Based OCT (SB-OCT) and a Swept Source OCT (SS-OCT) imaging system.

18. The method of claim 1, wherein the imaging of the eye comprises at least one of:
    creating a single z-scan;
    creating a planar z-scan;
    creating a z-scan along a scanning line; or
    creating a z-scan in a raster pattern, or
    a combination of the recited steps.

19. An imaging system for imaging an eye, comprising:
    a Spectral Domain Optical Coherence Tomographic (SD-OCT) imaging system that
       positions the eye relative to the SD-OCT imaging system,
          the eye having a first and a second structure;
       generates a first image-portion, selected from a direct image and a mirror image of the first structure;
       generates a second image-portion, selected from a direct image and a mirror image of the second structure; and suppresses non-selected images of the first and second structures.

20. The imaging system of claim 19, the SD-OCT imaging system comprising;
an imaging light source that outputs an imaging light;
one or more beam splitters that
splits the imaging light into an imaging beam and a. reference beam; and
unifies a returned imaging light-portion and a returned reference light-portion into an interfering light;
a reference device, that returns the reference light-portion, with a time difference proportional to a reference distance; and
an interference analyzer, that
receives the interfering light; and
generates an SD-OCT image of the eye.

21. The imaging system of claim 20, wherein:
the SD-OCT is one of a
Spectrometer Based OCT (SB-OCT) or a Swept Source OCT (SS-OCT).

22. The imaging system of claim 20, wherein:
the reference device is configured so that the returned reference light-portion is one of advanced or delayed relative to the returned imaging light-portion.

23. The imaging system of claim 20, wherein:
the reference distance of the reference mirror is related to a reference depth in the eye, wherein
the interference analyzer as a maximum imaging sensitivity at the reference depth.

24. The imaging system of claim 23, wherein:
the first structure is an anterior capsule layer of a lens of the eye;
the second structure is a posterior capsule layer of the lens of the eye;
the reference distance is adjustable to set the reference depth so that a depth-sequence of the first image-portion, the second image-portion and an image of a cornea is one of
mirror image of the posterior capsule layer—direct image of the anterior capsule layer—direct image of a cornea;
direct image of the anterior capsule layer—mirror image of the posterior capsule layer—direct image of the cornea; or
direct image of the anterior capsule layer—direct image of the cornea—mirror image of the posterior capsule layer.

25. The imaging system of claim 23, wherein:
the first structure is an anterior capsule layer of a lens of the eye;
the second structure is a posterior capsule layer of the lens of the eye;
the reference distance is adjustable to set the reference depth so that a depth-sequence of the first image-portion, the second image-portion and an image of a cornea is one of
direct image of the posterior capsule layer—mirror image of the anterior capsule layer—mirror image of a cornea;
mirror image of the anterior capsule layer13 direct image of the posterior capsule layer13 mirror image of the cornea; or
mirror image of the anterior capsule layer—mirror image of the cornea—direct image of the posterior capsule layer.

26. The imaging system of claim 23, wherein:
the reference distance is adjustable to control the reference depth to within the range of 2-15 mm.

27. The imaging system of claim 23, wherein:
the SD-OCT imaging system controls an imaging range around the reference depth into a range of one of 0 mm-15 mm and 5 mm-15 mm.

28. The imaging system of claim 19, wherein:
the SD-OCT imaging system suppresses the non-selected images by at least one of
preventing the display of generated non-selected images;
generating the non-selected images without displaying the non-selected images; or
performing a computational step to prevent the generation of the non-selected images, or
a combination of the recited functions.

29. A method of imaging an object, the method comprising the steps of:
positioning the object relative to a Spectral Domain Optical Coherence Tomographic (SD-OCT) imaging system,
the object comprising a high contrast structure in a low contrast medium;
generating an image of the high contrast structure with the SD-OCT imaging system, corresponding to one of a direct image and a mirror image of the high contrast structure; and
suppressing a non-selected image of the high contrast structure.

30. The method of claim 29, the generating the image of the high contrast structure step comprising:
adjusting a reference depth of the SD-OCT imaging system
to generate the image of the high contrast structure at an image depth so that the image of the high contrast structure is distinguishable from a first image of a first structure.

31. The method of claim 30, the adjusting the reference depth step comprising:
distinguishing the image of the high contrast structure from the first image by at least one of
recognizing a spatial separation of the image of the high contrast structure from the first image;
applying a pattern recognition approach;
distinguishing a signal characteristic of the image of the high contrast structure and the first image;
utilizing pre-existing knowledge about the object; or
utilizing a knowledge about the object based on a diagnostics.

32. The method of claim 29, the generating an image of the high contrast structure step comprising:
a homodyne imaging.

33. The method of claim 29, wherein the generating an image of the high contrast structure step comprises:
setting a reference depth of the SD-OCT imaging system; and
adjusting an imaging range around the reference depth
to result in the imaging range covering the high contrast structure.

34. The method of claim 33, wherein the adjusting the imaging range step comprises:
adjusting at least one of a central wavelength and a wavelength resolution of the SD-OCT imaging system
to result in the imaging range covering the high contrast structure.

35. The method of claim 33, wherein the adjusting the imaging range step comprises:
adjusting the imaging range to be within one of a range 0 mm-15 mm and 5 mm-15 mm.

36. The method of claim 33, wherein the adjusting the imaging range step comprises:
adjusting the reference depth to be within a range of 2 mm-15 mm.

37. The method of claim 33, wherein the adjusting the imaging range step comprises:
adjusting a focal depth of the SD-OCT imaging system; and
adjusting a Rayleigh range around the focal depth of the SD-OCT imaging system
to result in the imaging range being less than 4 times the Rayleigh range.

38. A surgical laser system, comprising:
a surgical laser delivery system; and
a Spectral Domain Optical Coherence Tomographic (SD-OCT) imaging system, coupled to the surgical laser delivery system, wherein
the SD-OCT imaging system
images an object having a high contrast structure in a low contrast medium;
generates an image of the high contrast structure corresponding to one of a direct image and a mirror image of the high contrast structure; and
suppresses a non-selected image of the high contrast structure.

39. The surgical laser system of claim 38, the SD-OCT imaging system comprising:
an imaging light source to output an imaging light;
one or more beam splitter that
splits the imaging light into an imaging beam and a reference beam; and
unifies a returned imaging beam-portion and a returned reference beam-portion into an interference beam;
a reference mirror, that returns the reference beam-portion, positioned at a reference distance; and
an interference analyzer, that
receives the interference beam; and
generates an SD-OCT image of the eye.

40. The imaging system of claim 39, wherein:
the SID-OCT is one of a
Spectrometer Based OCT (SB-OCT) and a Swept Source OCT (SS-OCT).

41. The imaging system of claim 39, wherein:
the reference distance of the reference mirror is related to a reference depth in the eye, wherein
the interference analyzer has a maximum imaging sensitivity at the reference depth.

42. The imaging system of claim 41, wherein:
the reference distance is adjustable to control the reference depth to within the range of 2-15 mm.

43. The imaging system of claim 41, wherein:
the SD-OCT imaging system is configured to control an imaging range around the reference depth into a range of one of
0 mm-15 mm and 5 mm-15 mm.

44. The imaging system of claim 38, wherein:
the SD-OCT imaging system suppresses the non-selected image by at least one of
preventing the display of generated non-selected image;
generating the non-selected images without displaying the non-selected image; or
performing a computational step to prevent the generation of the non-selected image.

* * * * *